US009549995B2

(12) United States Patent
Yang et al.

(10) Patent No.: US 9,549,995 B2
(45) Date of Patent: Jan. 24, 2017

(54) EFFICIENT SYNTHESIS OF ETHYLENEDICYSTEINE-SUGAR CONJUGATES FOR IMAGING AND THERAPY

(71) Applicant: Board of Regents, The University of Texas System, Austin, TX (US)

(72) Inventors: David J. Yang, Sugar Land, TX (US); Dong-Fang Yu, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 462 days.

(21) Appl. No.: 13/850,917

(22) Filed: Mar. 26, 2013

(65) Prior Publication Data

US 2013/0343995 A1    Dec. 26, 2013

Related U.S. Application Data

(60) Provisional application No. 61/615,684, filed on Mar. 26, 2012.

(51) Int. Cl.
| | | |
|---|---|---|
| C07D 417/12 | (2006.01) | |
| A61K 49/00 | (2006.01) | |
| A61K 51/04 | (2006.01) | |
| A61K 31/70 | (2006.01) | |
| A61K 45/06 | (2006.01) | |

(Continued)

(52) U.S. Cl.
CPC .......... *A61K 49/0004* (2013.01); *A61K 31/70* (2013.01); *A61K 31/7048* (2013.01); *A61K 45/06* (2013.01); *A61K 49/0002* (2013.01); *A61K 51/0491* (2013.01); *C07D 417/12* (2013.01); *C07H 13/04* (2013.01); *C07H 13/10* (2013.01)

(58) Field of Classification Search
None
See application file for complete search history.

(56) References Cited

U.S. PATENT DOCUMENTS

| | | | |
|---|---|---|---|
| 6,407,071 | B1 | 6/2002 | Rubin |
| 6,692,724 | B1 | 2/2004 | Yang et al. |

(Continued)

FOREIGN PATENT DOCUMENTS

| | | |
|---|---|---|
| WO | WO 2004/044227 | 5/2004 |
| WO | WO 2008/036067 | 3/2008 |
| WO | WO 2008/045604 | 4/2008 |

OTHER PUBLICATIONS

Lo, J. M., Lin, K. S., Kao, C. H., & Wang, S. J. (1999). Preparation of 99 Tc-Labeled L, L-Ethylenedicysteine Diethylester and Labeling to Leukocytes. 核子醫學雜誌 12(1), 29-37.*

(Continued)

*Primary Examiner* — Nissa Westerberg
(74) *Attorney, Agent, or Firm* — Parker Highlander PLLC

(57) ABSTRACT

Novel methods of synthesis of ethylenedicysteine-sugar conjugates and therapeutic and diagnostic applications of such conjugates are disclosed. Methods of synthesizing these conjugates in high purity are also presented as using starting materials such as thiazolidine carboxylic acid. Also disclosed are methods of imaging, treating and diagnosing disease in a subject using these conjugates prepared herein, such as methods of imaging a tumor within a subject and methods of diagnosing myocardial ischemia.

21 Claims, 18 Drawing Sheets

(51) Int. Cl.
A61K 31/7048 (2006.01)
C07H 13/04 (2006.01)
C07H 13/10 (2006.01)

(56) References Cited

U.S. PATENT DOCUMENTS

| | | |
|---|---|---|
| 7,067,111 B1 | 6/2006 | Yang et al. |
| 2005/0084448 A1* | 4/2005 | Yang et al. ............ 424/1.49 |
| 2009/0238756 A1 | 9/2009 | Kim et al. |
| 2010/0055035 A1 | 3/2010 | Yang et al. |

OTHER PUBLICATIONS

Ponpipom et al. Carbohydrate Research, 82, p. 141-148, 1980.*
Still et al. J Org Chem 43(14), p. 2923-2925, 1978.*
Chem 115—Birch Reduction, http://faculty.chemistry.harvard.edu/files/myers/files/8-birch_reduction.pdf, accessed Oct. 5, 2015.*
PCT International Search Report and Written Opinion issued in International Application No. PCT/US2013/033919, mailed Jul. 18, 2013.
Yang et al., "Imaging with 99mTc ECDG targeted at the multifunctional glucose transport system: feasibility study with rodents", *Radiology*, 226(2):465-73, 2003.
Extended European Search Report and Opinion issued in European Application No. 13767943.7, mailed Oct. 7, 2015.
Yan et al., "Antioxidative properties of a newly synthesized 2-glucosamine-thiazolidine-4(R)-carboxylic acid (GlcNH$_2$Cys) in mice," *Nutrition Research*, 26:369-377, 2006.
Zhang et al., "Molecular imaging of mesothelioma with $^{99m}$Tc-ECG and $^{68}$Ga-ECG," *Journal of Biomedicine and Biotechnology*, pp. 1-9, 2012.

* cited by examiner

EFFICIENT SYNTHESIS OF ETHYLENEDICYSTEINE-SUGAR CONJUGATES FOR IMAGING AND THERAPY

This application claims the benefit of U.S. Provisional Patent Application No. 61/615,684, filed Mar. 26, 2012, which is incorporated herein by reference in its entirety.

BACKGROUND OF THE INVENTIONS

1. Field of the Invention

The present invention relates generally to the fields of chemical synthesis, imaging, radiotherapy, labeling, chemotherapy, medical therapy, treatment of cardiovascular disease, and treatment of cancer. More particularly, the invention concerns novel methods of synthesis of conjugates for molecular imaging and therapy.

2. Description of Related Art

Regarding synthetic preparations of molecular agents for metal labeling, when such agents are prepared in aqueous (wet) conditions, purification of the agents can sometimes present a problem. Purification in aqueous conditions can be achieved using, for example, size exclusion chromatography, or dialysis with membranes of particular molecular weight cut-offs; for example, dialysis is typically most effective when separating species of molecular weights of 1000 g/mol or higher. However, this method of purification often isolates not only the desired agent, but also any other species that may pass through the membrane. Introduction of impurities into imaging agents may be problematic in future applications of the imaging agents, especially regarding imaging and/or therapeutic uses. For example, if an imaging agent incorporating a radionuclide (the "true" imaging agent) is thought to be pure but actually contains impurities that also incorporate a radionuclide, the proper measurement or detection of the "true" imaging agent may be obscured or rendered false due to the presence of the impurity.

Methods of synthesizing organic compounds in organic solvents and the use of protecting groups, typically offer improvements in the purification of compounds over aqueous purifications. The installation of protecting groups permits various functional groups of intermediates during the synthesis to be protected, and facilitates the purification of those intermediates. Various means of purification using organic solvents allow for separation and isolation of desired compounds, such as imaging agents, with very little impurities. Further, species of molecular weights under 1000 g/mol can often easily be purified using organic chemistry purification methods. In view of the benefits offered by organic synthesis and purification over aqueous purification, methods of organically synthesizing and purifying imaging agents would likely yield agents of higher purity than those obtained via aqueous purification. However, the addition and removal of protecting groups may incur additional costs and reduce efficiency and purify of the final products.

Thus, a need exists for the preparation of these and other agents using synthetic techniques to allow for agents of higher purities to be obtained in a more efficient way.

SUMMARY OF THE INVENTION

Aspects of the invention provide novel methods for preparing a thiazolidine-sugar conjugate and an ethylenedicysteine-sugar conjugate. For preparing a thiazolidine-sugar conjugate, the method may comprise admixing an amino sugar with a thiazolidine carboxylic acid, thereby producing the thiazolidine-sugar conjugate. For preparing an ethylenedicysteine-sugar conjugate, the method may further comprise reducing the thiazolidine-sugar conjugate with a reducing agent comprising an alkali metal and an electron source.

For example, the amino sugar is an amino hexose or an amino pentose. Non-limiting examples of the amino hexose include an amino derivative of glucose, galactose, mannose, idose, talose, altrose, allose, gulose or fructose. A particular example of the amino hexose is glucosamine. Non-limiting examples of the amino pentose include an amino derivative of ribose, xylose, arabinose or lyxose. The amino sugar is a sugar having an amino group located at the 2', 3', 4' or 5' position of the sugar. In a particular aspect, the amino sugar has an amino group positioned at the 2' position at the sugar ring.

The method of admixing may be carried out in an organic solvent, such as dimethylformamide, dimethylsulfoxide, dioxane, methanol, ethanol, hexane, methylene chloride, acetonitrile, tetrahydrofuran, or a mixture thereof. In other aspects, the method of admixing may be carried out in an aqueous solvent.

One, two, three, four, five or all of the hydroxyl groups of the amino sugar may be protected, for example, by an acetyl or benzoyl group, or unprotected. In a particular example, the amino sugar is glucosamine protected by acetyl groups, such as 1,3,4,6-tetra-O-acetyl-2-amino-α-D-glucopyranose hydrochloride. Protecting groups are usually used in organic synthesis and not aqueous synthesis.

Methods of the present invention may further comprise at least one purification step. Any compound of the present invention may be purified via any method known to those of skill in the art. Persons of skill in the art are familiar with such methods, and when those methods may be employed. For example, in a multi-step synthesis that is aimed at arriving at a particular compound, a purification step may be performed after every synthetic step, after every few steps, at various points during the synthesis, and/or at the very end of the synthesis. In some methods, one or more purification steps comprises technique selected from the group consisting of silica gel column chromatography, HPLC (high-performance liquid chromatography) and LC (liquid chromatography). In certain embodiments, purification methods specifically exclude size exclusion chromatography and/or dialysis. Methods of purification are described in more detail below. In a particular aspect, the method may comprise purifying the thiazolidine-sugar conjugate prior to the reduction.

For preparing an ethylenedicysteine-sugar conjugate, the thiazolidine-sugar conjugate may be reduced by an alkali metal and an electron source. The alkali metal may be lithium, sodium or potassium. The electron source may be liquid ammonia, methylamine, ethylamine or ethylenediamine. In a particular aspect, the reduction may be a Birch reduction.

To generate a metal ion labeled-ethylenedicysteine(EC)-sugar conjugate, the method may further comprise chelating a metal ion to the ethylenedicysteine-sugar conjugate. For example, the metal ion is selected from the group of metal ions consisting of a technetium ion, a stannous ion, a copper ion, an indium ion, a thallium ion, a gallium ion, an arsenic ion, a rhenium ion, a holmium ion, a yttrium ion, a samarium ion, a selenium ion, a strontium ion, a gadolinium ion, a bismuth ion, an iron ion, a manganese ion, a lutecium ion, a cobalt ion, a platinum ion, a calcium ion and a rhodium ion. In some aspects, the metal ion is a radionuclide, and any radionuclide known to those of skill in art. The non-limiting examples of radionucleodies include $^{99m}$Tc, $^{117m}$Sn, $^{177}$Lu, $^{188}$Re, $^{186}$Re, $^{153}$Sm, $^{166}$Ho, $^{90}$Y, $^{89}$Sr, $^{67}$Ga, $^{68}$Ga, $^{111}$In, $^{183}$Gd, $^{59}$Fe, $^{225}$Ac, $^{212}$Bi, $^{211}$At, $^{45}$Ti, $^{60}$Cu, $^{61}$Cu, $^{67}$Cu, $^{64}$Cu and $^{62}$Cu. In other aspects, the metal ion is a nonradioactive metal such as $^{187}$Re.

Further embodiments of the invention concern methods of imaging a site, diagnosing a disease, or treating a disease within a subject comprising. The method may comprise obtaining a metal ion labeled-ethylenedicysteine(EC)-sugar conjugate prepared as described herein and administering to the subject a pharmaceutically or diagnostically effective amount of a metal ion labeled-ethylenedicysteine(EC)-sugar conjugate, wherein the site is imaged, the disease is diagnosed, or the disease is treated.

The site to be imaged may be a tumor. The method may be further defined as a method of treating a subject with cancer. In particular aspects, the cancer is breast cancer, lung cancer, prostate cancer, ovarian cancer, brain cancer, liver cancer, cervical cancer, colon cancer, renal cancer, skin cancer, head and neck cancer, bone cancer, a esophageal cancer, bladder cancer, uterine cancer, lymphatic cancer, stomach cancer, pancreatic cancer, testicular cancer, lymphoma, or leukemia.

In further aspects, the method may be further defined as a method of imaging a site within a subject comprising detecting a signal from metal ion labeled-ethylenedicysteine (EC)-sugar conjugate that is localized at the site. The signal may be detected using a technique selected from the group consisting of PET, PET/CT, CT, SPECT, SPECT/CT, MRI, PET/MRI, SPECT/MRI, optical imaging and ultrasound.

The site to be imaged may be a tumor a heart. The method may be further defined as a method of imaging, diagnosing, or treating a subject with a cardiovascular disease. The cardiovascular disease may be a myocardial infarction, congestive heart failure, cardiomyopathy, valvular heart disease, an arrhythmia, congenital heart disease, angina pectoris, noncardiac circulatory congestion, systolic heart failure, heart failure with normal systolic function, or right-sided heart failure.

In a further embodiment a conjugate composition or kit is provided comprising an ethylenedicysteine-sugar conjugate according to the embodiments and neomycin. In some aspects, the composition comprises about 0.1 mg to about 1.0 mg of neomycin per 1 mg of ethylenedicysteine-sugar conjugate (e.g., about 0.2-0.8, 0.3-0.7, 0.4-0.6 or about 0.5 mgs per 1 mg of ethylenedicysteine-sugar conjugate). In still further aspects the composition may further comprise antioxidants, stabilizing agents, preservatives or salts. For example, a composition can additionally comprise ascorbic acid, cysteine, and/or Tin(II) chloride. In some specific aspects a composition comprises (a) about 0.5 to 2.0 mg of ascorbic acid per 1 mg of ethylenedicysteine-sugar conjugate; (b) about 0.1 to 1.0 mg of cysteine per 1 mg of ethylenedicysteine-sugar conjugate; and/or (c) about 0.05 to 0.5 mg of Tin(II) chloride per 1 mg of ethylenedicysteine-sugar conjugate. In some aspects the composition is an aqueous solution or a solution that has been frozen and/or lyophilized.

In a related embodiment there is provided a method of making a conjugate composition comprising (a) dissolving an ethylenedicysteine-sugar conjugate and neomycin in aqueous solution (e.g., a Tin(II) chloride solution); and (b) lyophilizing or freezing the solution to provide a ethylenedicysteine-sugar conjugate composition. Likewise, there is provided a method of making a metal chelate of a ethylenedicysteine-sugar conjugate comprising mixing a solution comprising the ethylenedicysteine-sugar conjugate and neomycin with a metal ion (e.g., a radioactive metal ion) under appropriate conditions to form a chelate.

In still a further embodiment there is provided a method of imaging a site, diagnosing a disease, or treating a disease within a subject comprising administering a metal ion labeled-ethylenedicysteine (EC)-sugar conjugate to a patient in conjunction with neomycin. For example, the method can comprise (a) obtaining a composition comprising metal ion labeled-ethylenedicysteine (EC)-sugar conjugate and neomycin; and (b) administering to the subject a pharmaceutically or diagnostically effective amount of the composition, wherein the site is imaged, the disease is diagnosed, or the disease is treated.

In still a further embodiment a composition is provided comprising a metal ion labeled-ethylenedicysteine-sugar conjugate and neomycin (e.g., about 0.1 mg to about 1.0 mg of neomycin per 1 mg of ethylenedicysteine-sugar conjugate). For instance, in some aspects the composition is for use in imaging a site, diagnosing a disease, or treating a disease within a subject.

Embodiments discussed in the context of methods and/or compositions of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following figures form part of the present specification and are included to further demonstrate certain aspects of the invention. The invention may be better understood by reference to one or more of these drawings in combination with the detailed description of specific embodiments presented herein.

DETAILED DESCRIPTION OF THE PREFERRED EMBODIMENTS

Figure 1:
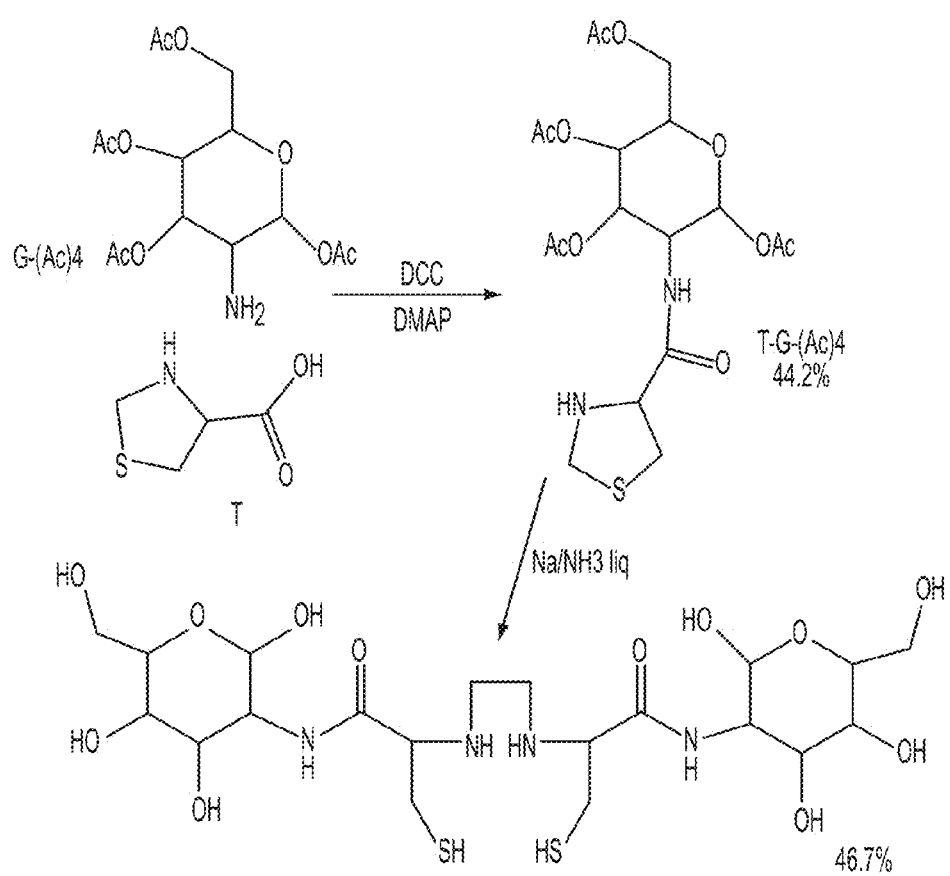
FIG. 1. Efficient Synthesis of ECG.

The present invention concern novel synthetic methods for the preparation of a thiazolidine-sugar conjugate as precursors to prepare an ethylenedicysteine-sugar conjugate. The present invention further provides synthetic methods of an ethylenedicysteine-sugar conjugate. In some aspects these synthetic methods may obviate the need of adding protecting groups to ethylenedicysteine (EC) and increase process efficiency and purify of the final products as compared to other methods as described in U.S. Patent Publn. No. 20100055035 (incorporated herein by reference).

In certain aspects, at least a part of the methods of the present invention take place in an organic solvent. Solvent choices for the methods of the present invention will be known to one of ordinary skill in the art. Solvent choices may depend, for example, on which one(s) will facilitate the solubilizing of all the reagents, or, for example, which one(s) will best facilitate the desired reaction (particularly if the mechanism of the reaction is known). Solvents may include, for example, polar solvents and/or non-polar solvents. A solvent may be a polar aprotic solvent, such as dimethylsulfoxide. Solvents choices include, but are not limited to, dimethylformamide, dimethylsulfoxide, dioxane, methanol, ethanol, hexane, methylene chloride, tetrahydrofuran, and/or acetonitrile. In some embodiments, solve its include ethanol, dimethylformamide and/or dioxane. More than one solvent may be chosen for any particular reaction or purification procedure. Water may also be admixed into any solvent choice; this can be done to enhance the solubility of one or more reactants, for example. Methods based on wet (aqueous) chemistry are also provided.

As described herein, some aspects of the invention involve the use of protection groups to protect the amino sugar in its reaction with thiazolidine or its derivatives. However, aspects of the invention may obviate the need for adding protection groups to ethylenedicysteine (EC) as in U.S. Patent Pubin. No. 20100055035.

When a chemical reaction is to be carried out selectively at one reactive site in a multifunctional compound, other reactive sites must be temporarily blocked. A "protecting group," or "protected-nucleophilic group" as used herein, is defined as a group used for the purpose of this temporary blockage. During the synthesis of the macromolecules of the present invention, various functional groups must be protected using protecting groups (or protecting agents) at various stages of the synthesis. There are a number of methods well known to those skilled in the art for accomplishing such a step. For protecting agents, their reactivity, installation and use, see, e.g., Greene and Wuts (1999), herein incorporated by reference in its entirety. The function of a protecting group is to protect one or more functionalities (e.g., —NH2, —SH, —COOH) during subsequent reactions which would not proceed well, either because the free (in other words, unprotected) functional group would react and be functionalized in a way that is inconsistent with its need to be free for subsequent reactions, or the free functional group would interfere in the reaction. The same protecting group may be used to protect one or more of the same or different functional group(s). Also, different protecting groups can be used to protect the same type of functional group within a macromolecule of the present invention in multiple steps.

In particular aspects, the hydroxyl groups of the amino sugar as the starting material may be protected. Hydroxy (or alcohol) protecting groups are well known to those skilled in the art. See, for example, Greene and Wuts (1999), Chapter 2. These protecting groups can be installed via protecting agents well known to those of skill in the art. Removal of these groups is also well known to those of skill in the art.

A suitable hydroxy protecting group may be selected from the group consisting of esters or ethers. Esters such as acetate, benzoyl, tert-butylcarbonyl and trifluoroacetyl groups are removable by acidic or basic conditions. Ethers such as methoxy, ethoxy and tri-benzylmethyl are removable by stronger acidic or basic conditions. A preferred protecting group is an acetate ester.

The present invention contemplates methods for admixing an amino sugar with a thiazolidine carboxylic acid. The condition for admixing may include any conditions suitable to form a peptide bond between the amino sugar and the thiazolidine carboxylic acid, such as one or more coupling agents or catalysts. Coupling agents, as used herein, are reagents used to facilitate the coupling of an amino group and a carboxylic group to form a peptide bond. Such agents are well known to those of ordinary skill in the art and may be employed in certain embodiments of methods of the present invention. Examples of coupling, agents include, but are not limited to, sulfa-N-hydroxysuccinimide (sulfo-NHS), dimethylaminopyridine (DMAP), diazabicyclo[5.4.0]undec-7-ene (DBU), 1-ethyl-3-(3-dimethylaminopropyl)carbodiimide (EDA) and dicyclohexylcarbodiimide (DCC). Other carbodiimides are also envisioned as coupling agents, Coupling agents are discussed, for example, in Bodansky, 1993 and Grant, 1992. These coupling agents may be used singly or in combination with each other or other agents to facilitate conjugation. The conjugated product may then be purified by, for example, silica gel column chromatography or HPLC.

In some aspects of the invention, there is no need for a separate deprotection reaction. The reduction reaction can remove protection groups while converting the thiazolidine-sugar conjugate to an ethylenedicysteine-sugar conjugate. The reduction reaction comprise the use of a reducing agent comprising an alkali metal and an electron source, e.g. a Lewis base. The alkali metal may be lithium, sodium or potassium. The electron source may be a Lewis base such as liquid ammonia, methylamine, ethylamine or ethylenediamine. In a particular aspect, the reduction may be a Birch reduction. For example, the reducing agent for the Birch reduction comprises lithium or sodium metal and liquid ammonia. In alternative embodiments, the reducing agent comprises lithium metal, sodium metal, potassium metal, or calcium metal and methylamine or ethylamine. The Birch reduction reaction mixture may include a solvent mixture. This solvent mixture may comprises isopropyl alcohol (IPA), t-butyl alcohol, tetrahydrofuran (THF), ammonia, or combinations thereof. Depending on the reagents used, the Birch reduction may occur at a temperature of from about −80° C. to about 55° C. When liquid ammonia is used as a reagent, the reduction may take place at about −80° C. to about −35° C. When methylamine or ethylamine is used as a reagent, the reduction may take place at a temperature from about −10° C. to about 10° C. The Birch reduction reaction mixture is maintained at the above temperatures for about 10 minutes to about 4 hours.

As mentioned above, persons of ordinary skill in the art will be familiar with methods of purifying compounds of the present invention. As used herein, "purification" refers to any measurable increase in purity relative to the purity of the material before purification. Purification of every compound of the present invention is generally possible, including the purification of intermediates as well as purification of the final products. The purification step is not always included in the general methodologies explained below, but one of ordinary skill in the art will understand that compounds can generally be purified at any step. Examples of purification methods include gel filtration, size exclusion chromatography (also called gel filtration chromatography, gel permeation chromatography or molecular exclusion), dialysis, recrystallization, sublimation, derivatization, electrophoresis, silica gel column chromatography and high-performance liquid chromatography (HPLC), including normal-phase HPLC and reverse-phase HPLC. In certain embodiments, size exclusion chromatography and/or dialysis are specifically excluded as forms of purification of compounds of the present invention. Purification of compounds via silica gel column chromatography or HPLC, for example, offer the benefit of yielding desired compounds in very high purity, often higher than when compounds are purified via other methods. Radiochemical purity of compounds of the present invention can also be determined. Methods of determining radiochemical purity are well-known in the art and include chromatographic methods in conjunction with radioactivity detection methods (e.g., autoradiography analyses). Examples of comparisons of purity of compounds made via organic and wet methodologies and purified by varying methods are provided below.

Methods of determining the purity of compounds are well known to those of skill in the art and include, in non-limiting examples, autoradiography, mass spectroscopy, melting point determination, ultra violet analysis, calorimetric analysis, (HPLC), thin-layer chromatography and nuclear magnetic resonance (NMR) analysis (including, but not limited to, $^1$H and $^{13}$C NMR). In some embodiments, a calorimetric method could be used to titrate the purity of intermediates or final products. In one embodiment, the purity of an unknown compound may be determined by comparing it to a compound of known purity: this comparison may be in the form of a ratio whose measurement describes the purity of the unknown. Software available on varying instruments spectrophotometers, (HPLCs, NMRs) can aid one of skill in the art in making these determinations, as well as other means known to those of skill in the art.

The present invention further contemplates methods for the chelation (also called coordination) of one or more metal ions to the ethylenedicysteine-sugar conjugate to generate a metal ion labeled-ethylenedicysteine(EC)-sugar conjugate. Such chelation steps may take place in an organic solvent. In other embodiments, chelation takes place in aqueous media. In certain embodiments, the chelator EC and the sugar may each contribute to the chelation of the metal ion. In preferred embodiments, the metal ion is chelated only to the chelator EC. The chelated metal ion may be bound via, (hr example, an ionic bond, a covalent, bond, or a coordinate covalent bond (also called a dative bond). Methods of such coordination are well known to those of ordinary skill in the art. In one embodiment, coordination may occur by admixing a metal ion into a solution containing the ethylenedicysteine-sugar conjugate. In another embodiment, coordination may occur by admixing a metal ion into a solution containing a EC-sugar conjugate.

In some non-limiting examples, the metal ion may be technetium, indium, rhenium, gallium, copper, holmium, platinum, gadolinium, lutetium, yttrium, cobalt, calcium, arsenic, or any isotope thereof. Any metal ion described herein may be chelated to a compound of the present invention.

Certain aspects of the present invention pertain to compositions wherein a therapeutic moiety is conjugated to a chelator conjugate of the present invention, such as an ethylenedicysteine-sugar conjugate. The composition of the present invention may, in certain embodiments, be useful in dual imaging and therapy. In certain particular embodiments, the therapeutic moiety is a moiety that is an agent known or suspected to be of benefit in the treatment or prevention of hyperproliferative disease in a subject. The subject may be an animal, such as a mammal. In certain particular embodiments, the subject is a human.

In other embodiments of the present invention, the therapeutic moiety is a therapeutic metal ion (e.g., Re-188, Re-187, Re-186, Ho-166, Y-90, Sr-89, and Sm-153), and the metal-chelated ethylenedicysteine-sugar conjugate is an agent that is a therapeutic agent (rather than an imaging agent) that can be applied in the treatment or prevention of a hyperproliferative disease.

A hyperproliferative disease is herein defined as any disease associated with abnormal cell growth or abnormal cell turnover. For example, the hyperproliferative disease may be cancer. The term "cancer" as used herein is defined as an uncontrolled and progressive growth of cells in a tissue. A skilled artisan is aware other synonymous terms exist, such as neoplasm or malignancy or tumor. Any type of cancer is contemplated for treatment by the methods of the present invention. For example, the cancer may be breast cancer, lung cancer, ovarian cancer, brain cancer, liver cancer, cervical cancer, colon cancer, renal cancer, skin cancer, head and neck cancer, bone cancer, esophageal cancer, bladder cancer, uterine cancer, stomach cancer, pancreatic cancer, testicular cancer, lymphoma, or leukemia. In other embodiments of the present invention, the cancer is metastatic cancer.

In certain embodiments of the present invention, the compositions of the present invention are suitable for dual chemotherapy and radiation therapy (radiochemotherapy). For example, the chelator EC-sugar conjugate as set forth herein may be chelated to a metal ion that is a therapeutic metal ion, as well as a therapeutic moiety (such as an anti-cancer moiety). As another example, a therapeutic metal ion may be chelated to both the EC and the sugar moiety in the EC-sugar conjugate.

For example, the metal ion may be a beta-emitter. As herein defined, a beta emitter is any agent that emits beta energy of any range. Examples of beta emitters include Re-188, Re-187, Re-186, Ho-166, Y-90, and Sn-153. One of ordinary skill in the art would be familiar with agents for use in the treatment of hyperproliferative disease, such as cancer.

One of ordinary skill in the art would be familiar with the design of chemotherapeutic protocols and radiation therapy protocols that can applied in the administration of the compounds of the present invention. As set forth below, these agents may be used in combination with other therapeutic modalities directed at treatment of a hyperproliferative disease, such as cancer. Furthermore, one of ordinary skill in the art would be familiar with selecting an appropriate dose for administration to the subject. The protocol may involve a single dose, or multiple doses. The patient would be monitored for toxicity and response to treatment using protocols familiar to those of ordinary skill in the art.

Pharmaceutical compositions of the present invention comprise a therapeutically or diagnostically effective amount of a composition of the present invention. The phrases "pharmaceutical or pharmacologically acceptable" or "therapeutically effective" or "diagnostically effective" refers to molecular entities and compositions that do not produce an adverse, allergic or other untoward reaction when administered to an animal, such as, for example, a human, as appropriate. The preparation of therapeutically effective or diagnostically effective compositions will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by the FDA Office of Biological Standards.

As used herein, "a composition comprising a therapeutically effective amount" or "a composition comprising a diagnostically effective amount" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. Except insofar as any conventional carrier is incompatible with the active ingredient, its use in the present compositions is contemplated.

The compositions of the present invention may comprise different types of carriers depending on whether it is to be administered in solid, liquid or aerosol form, and whether it need to be sterile for such routes of administration as injection. The compositions of the present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), or by other method or any combination of the forgoing as would be known to one of ordinary skill in the art.

The actual required amount of a composition of the present invention administered to a patient can be determined by physical and physiological factors such as body weight, severity of condition, the tissue to be imaged, the type of disease being treated, previous or concurrent imaging or therapeutic interventions, idiopathy of the patient, and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of the chelator-metal ion chelate. In other embodiments, the an active compound may comprise between about 2% to about 75% of the weight of the unit, or between about 25% to about 60%, for example, and any range derivable therein. In other non-limiting examples, a dose may also comprise from about 0.1 mg/kg/body weight to about 1000 mg/kg/body weight or any amount within this range, or any amount greater than 1000 mg/kg/body weight per administration.

In any case, the composition may comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal or combinations thereof.

The compositions of the present invention may be formulated in a free base, neutral or salt form. Pharmaceutically acceptable salts include the salts formed with the free carboxyl groups derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

Sterile injectable solutions may be prepared using techniques such as filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO (dimethylsulfoxide) as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

The compositions of the present invention may be used in a variety of nuclear medicine techniques for imaging known to those of ordinary skill in the art. For example, gamma camera imaging is contemplated as a method of imaging that can be utilized for measuring a signal derived from the metal ion chelated to the EC-sugar conjugate. One of ordinary skill in the art would be familiar with techniques for application of gamma camera imaging (see, e.g., Kundra et al., 2002, herein specifically incorporated by reference).

Radionuclide imaging modalities (positron emission tomography, (PET); single photon emission computed tomography (SPECT)) are diagnostic cross-sectional imaging techniques that map the location and concentration of radionuclide-labeled radiotracers. Although CT and MRI provide considerable anatomic information about the location and the extent of tumors, these imaging modalities cannot adequately differentiate invasive lesions from edema, radiation necrosis, grading or gliosis. PET and SPECT can be used to localize and characterize tumors by measuring metabolic activity.

PET and SPECT provide information pertaining to information at the cellular level, such as cellular viability. In PET, a patient ingests or is injected with a slightly radioactive substance that emits positrons, which can be monitored as the substance moves through the body. In one common application, for instance, patients are given glucose with positron emitters attached, and their brains are monitored as they perform various tasks. Since the brain uses glucose as it works, a PET image shows where brain activity is high.

Closely related to PET is single-photon emission computed tomography, or SPECT. The major difference between the two is that instead of a positron-emitting substance, SPECT uses a radioactive tracer that emits low-energy photons. SPECT is valuable for diagnosing coronary artery disease, and already some 2.5 million SPECT heart studies are done in the United States each year.

PET radiopharmaceuticals for imaging are commonly labeled with positron-emitters such as $^{11}$C, $^{13}$N, $^{15}$O, $^{18}$F, $^{82}$Rb, $^{62}$Cu, and $^{68}$Ga. SPECT radiopharmaceuticals are commonly labeled with positron emitters such as $^{99m}$Tc, $^{201}$Tl, and $^{67}$Ga. Regarding brain imaging, PET and SPECT radiopharmaceuticals are classified according to blood-brain-barrier permeability (BBB), cerebral perfusion and metabolism receptor-binding, and antigen-antibody binding (Saha et al., 1994). The blood-brain-barrier SPECT agents, such as $^{99m}$TcO4-DTPA, $^{201}$Tl, and [$^{67}$Ga]citrate are excluded by normal brain cells, but enter into tumor cells because of altered BBB. SPECT perfusion agents such as [$^{123}$I]IMP, [$^{99m}$Tc]HMPAO, [$^{99m}$Tc]ECD are lipophilic agents, and therefore diffuse into the normal brain. Important receptor-binding SPECT radiopharmaceuticals include [$^{123}$I]QNE, [$^{123}$I]IBZM, and [$^{123}$I]iomazenil. These tracers bind to specific receptors, and are of importance in the evaluation of receptor-related diseases.

Computerized tomography (CT) is contemplated as an imaging modality in the context of the present invention. By taking a series of X-rays, sometimes more than a thousand, from various angles and then combining them with a computer, CT made it possible to build up a three-dimensional image of any part of the body. A computer is programmed to display two-dimensional slices from any angle and at any depth.

In CT, intravenous injection of a radiopaque contrast agent can assist in the identification and delineation of soft tissue masses when initial CT scans are not diagnostic. Similarly, contrast agents aid in assessing the vascularity of a soft tissue or bone lesion. For example, the use of contrast agents may aid the delineation of the relationship of a tumor and adjacent vascular structures.

CT contrast agents include, for example, iodinated contrast media. Examples of these agents include iothalamate, iohexol, diatrizoate, iopamidol, ethiodol and iopanoate. Gadolinium agents have also been reported to be of use as a CT contrast agent (see, e.g., Henson et al., 2004). For example, gadopentate agents have been used as a CT contrast agent (discussed in Strunk and Schild, 2004).

Magnetic resonance imaging (MRI) is an imaging modality that is newer than CT that uses a high-strength magnet and radio-frequency signals to produce images. The most abundant molecular species in biological tissues is water. It is the quantum mechanical "spin" of the water proton nuclei that ultimately gives rise to the signal in imaging experiments. In MRI, the sample to be imaged is placed in a strong static magnetic field (1-12 Tesla) and the spins are excited with a pulse of radio frequency (RF) radiation to produce a net magnetization in the sample. Various magnetic field gradients and other RF pulses then act on the spins to code spatial information into the recorded signals. By collecting and analyzing these signals, it is possible to compute a three-dimensional image which, like a CT image, is normally displayed in two-dimensional slices.

Contrast agents used in MR imaging differ from those used in other imaging techniques. Their purpose is to aid in distinguishing between tissue components with identical signal characteristics and to shorten the relaxation times (which will produce a stronger signal on T1-weighted spin-echo MR images and a less intense signal on T2-weighted images). Examples of MRI contrast agents include gadolinium chelates, manganese chelates, chromium chelates, and iron particles.

Both CT and MRI provide anatomical information that aid in distinguishing tissue boundaries and vascular structure. Compared to CT, the disadvantages of MRI include lower patient tolerance, contraindications in pacemakers and certain other implanted metallic devices, and artifacts related to multiple causes, not the least of which is motion (Alberico et al., 2004). CT, on the other hand, is fast, well tolerated, and readily available but has lower contrast resolution than MRI and requires iodinated contrast and ionizing radiation (Alberico et al., 2004). A disadvantage of both CT and MRI is that neither imaging modality provides functional information at the cellular level. For example, neither modality provides information regarding cellular viability.

Optical imaging is another imaging modality that has gained widespread acceptance in particular areas of medicine. Examples include optical labelling of cellular components, and angiography such as fluorescein angiography and indocyanine green angiography. Examples of optical imaging agents include, for example, fluorescein, a fluorescein derivative, indocyanine green, Oregon green, a derivative of Oregon green derivative, rhodamine green, a derivative of rhodamine green, an eosin, an erythrosin, Texas red, a derivative of Texas red, malachite green, nanogold sulfosuccinimidyl ester, cascade blue, a coumarin derivative, a naphthalene, a pyridyloxazole derivative, cascade yellow dye, or dapoxyl dye.

Another biomedical imaging modality that has gained widespread acceptance is ultrasound. Ultrasound imaging has been used noninvasively to provide realtime cross-sectional and even three-dimensional images of soft tissue structures and blood flow information in the body. High-frequency sound waves and a computer to create images of blood vessels, tissues and organs.

Ultrasound imaging of blood flow can be limited by a number of factors such as size and depth of the blood vessel. Ultrasonic contrast agents, a relatively recent development, include perfluorine and perfluorine analogs, which are designed to overcome these limitations by helping to enhance grey-scale images and Doppler signals.

Certain embodiments of the present invention pertain to methods of imaging a site within a subject using two imaging modalities that involve measuring a first signal and a second signal from the imaging moiety-chelator-metal ion complex. The first signal is derived from the metal ion and the second signal is derived from the imaging moiety. As set forth above, any imaging modality known to those of ordinary skill in the art can be applied in these embodiments of the present imaging methods.

The imaging modalities are performed at any time during or after administration of the composition comprising the diagnostically effective amount of the composition of the present invention. For example, the imaging studies may be performed during administration of the dual imaging composition of the present invention, or at any time thereafter. In some embodiments, the first imaging modality is performed beginning concurrently with the administration of the dual imaging agent, or about 1 sec, 1 hour, 1 day, or any longer period of time following administration of the dual imaging agent, or at any time in between any of these stated times.

The second imaging modality may be performed concurrently with the first imaging modality, or at any time following the first imaging modality. For example, the second imaging modality may be performed about 1 sec, about 1 hour, about 1 day, or any longer period of time following completion of the first imaging modality, or at any time in between any of these stated times. In certain embodiments of the present invention, the first and second imaging modalities are performed concurrently such that they begin at the same time following administration of the agent. One of ordinary skill in the art would be familiar with performance of the various imaging modalities contemplated by the present invention.

In some embodiments of the present methods of dual imaging, the same imaging device is used to perform a first imaging modality and a second imaging modality. In other embodiments, a different imaging device is used to perform the second imaging modality. One of ordinary skill in the art would be familiar with the imaging devices that are available for performance of a first imaging modality and a second imaging modality, and the skilled artisan would be familiar with use of these devices to generate images. More details of the diagnostic and therapeutic methods may be found in US 2008/0107198 (incorporated herein by reference).

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Synthesis of N,N-Ethylenedicysteine-Glucosamine (EC-G). See FIG. 1.

General

All chemicals and solvents were obtained from Sigma-Aldrich (St. Louis, Mo.). Nuclear magnetic resonance (NMR) was performed on Bruker 300 MHz Spectrometer, and mass spectra were performed on Waters Q-TOF Ultima Mass Spectrometer (Milford, Mass.) at the core facility at the University of Texas MD Anderson Cancer Center (UTM-DACC; Houston, Tex.). Chemical shifts were reported in δ (ppm) and J values in Hertz. FDG was obtained from Department of Nuclear Medicine at UTMDACC.

Synthesis of ECG

Step 1. Synthesis of T-G-$(Ac)_4$

To a solution of thiazolidine-4-carboxylic acid (T) (2.6 g, 0.02 mol) in DMF (20 ml) and 5.0 ml trimethylamine, 1-hydroxybenzotriazole hydrate 2.7 g (0.02 mol) was added. After 30 min, 1,3,4,6-tetra-O-acetyl-2-amino-α-D-glucopyranose hydrochloride (G-$(Ac)_4$) (7.7 g, 0.02 mol), N,N'-dicyclohexylcarbodiimide (DCC; 4.2 g, 0.02 mol) and 4-dimethylaminopyridine (DMAP; 1.2 g, 0.01 mol) were added to the mixture and stirred for overnight at room temperature. The solution was evaporated to dryness at high vacuum. Dichloromethane ($CH_2Cl_2$) (50 ml) was added to the residual and kept at 4° C. for overnight, then filtered. The product was purified with silica gel by eluting with $CH_2Cl_2$/MeOH (95/5, V/V) to yield white product T-G-$(Ac)_4$ 4.08 g (44.2%). NMR and mass spectrometry were used to confirm the structure of T-G-$(Ac)_4$.

Step 2. Reduction Reaction

Sodium was added piece by piece to a solution of T-G-(Ac)4 (4.08 g, 8.8 mmol) in liquid ammonia (170 g). The color of the solution was slowly changed to dark blue. After 30 minutes, a small amount of ammonium chloride was added. The liquid ammonia was removed by reduced pressure. The residual solid was triturated with methanol (100 ml). The solid was then filtered and washed with additional methanol (50 ml) to yield crude product 4.16 g. To obtain analytical pure ECG, the crude product (0.1 g) was dissolved in 1.0 ml of HCl (0.1 N) and purified with Sephadex column by eluting with $H_2O$. The aqueous fractions were combined and lyophilized to yield EC-G 0.029 g (46.7%). NMR, mass spectrometry and HPLC were used to confirm the structure of ECG.

Results

The synthetic scheme is shown in FIG. 1. ECG was synthesized by two step reactions. In the first step, thiazolidine-4-carboxylic acid (T) was reacted with 1,3,4,6-tetra-O-acetyl-2-amino-α-D-glucopyranose hydrochloride (G-$(Ac)_4$) in the presence of 1-hydroxybenzotriazole hydrate, DCC and DMAP. After purification, the yield of product T-G-$(Ac)_4$ was 44.2%. $^1H$ NMR ($D_2O$, δ): 1.97-2.14(m, 12H), 3.88(t, 1H), 3.93 (s, 2H,), 4.05-4.10 (m, 6H) 4.22-4.30 (m, 2H,), 5.09 (t, 1H), 5.34 (t, 1H), 5.80(d, 1H ), 6.93(d, 1H,). $^{13}C$ NMR($D_2O$, δ): 171.19, 171.00, 170.65, 169.35, 166.35, 141.76, 92.05, 82.45, 72.79, 72.02, 68.02, 61.73, 60.39, 53.21, 42.32, 20.84, 20.68, 20.58, 20.55. FAB MS m/z: 462.5.

In the second step, T-G-$(Ac)_4$ was reduced by sodium in liquid ammonia (Birch reduction). The crude product was purified with a Sephadex column to yield ECG (46.7%). HPLC shows purity is over 82%. $^1H$ NMR (D2O, δ): 3.15-3.20 (m, 4H), 3.78-4.05 (m, 6H), 4.08-4.15 (m, 8H), 4.2-4.3 (d, 2H), 4.68-4.73 (d, 2H), 5.19-5.21 (d, 2H). $^{13}C$ NMR ($D_2O$, δ): 174.81, 174.56, 94.95, 90.87, 90.84, 75.96, 73.91, 73.85, 71.59, 70.71, 70.66, 70.10, 69.88, 60.72, 60.62, 56.72, 54.11, 23.33, 22.23, 21.96. FAB MS m/z: 591.

Example 2

Synthesis of Cold Ga-ECG $^{69}GaCl_3$ (20 mg, 0.11 mmol) in 0.2 ml $H_2O$ was added to a solution of ECG (60 mg, 0.1 mmol) in 0.5 ml $H_2O$. The pH value was adjusted to 4-5 with 0.1 N NaOH (50 μl). The solution was heated for 30 min at 60° C. The product was purified by a Sephadex column eluting with $H_2O$ to yield Ga-ECG. After lyophilization, Ga-ECG was obtained as white solid (52 mg, 78.1%). NMR, mass spectrometry, and HPLC were used to confirm the structure of $^{69}$Ga-ECG.

Figure 2:
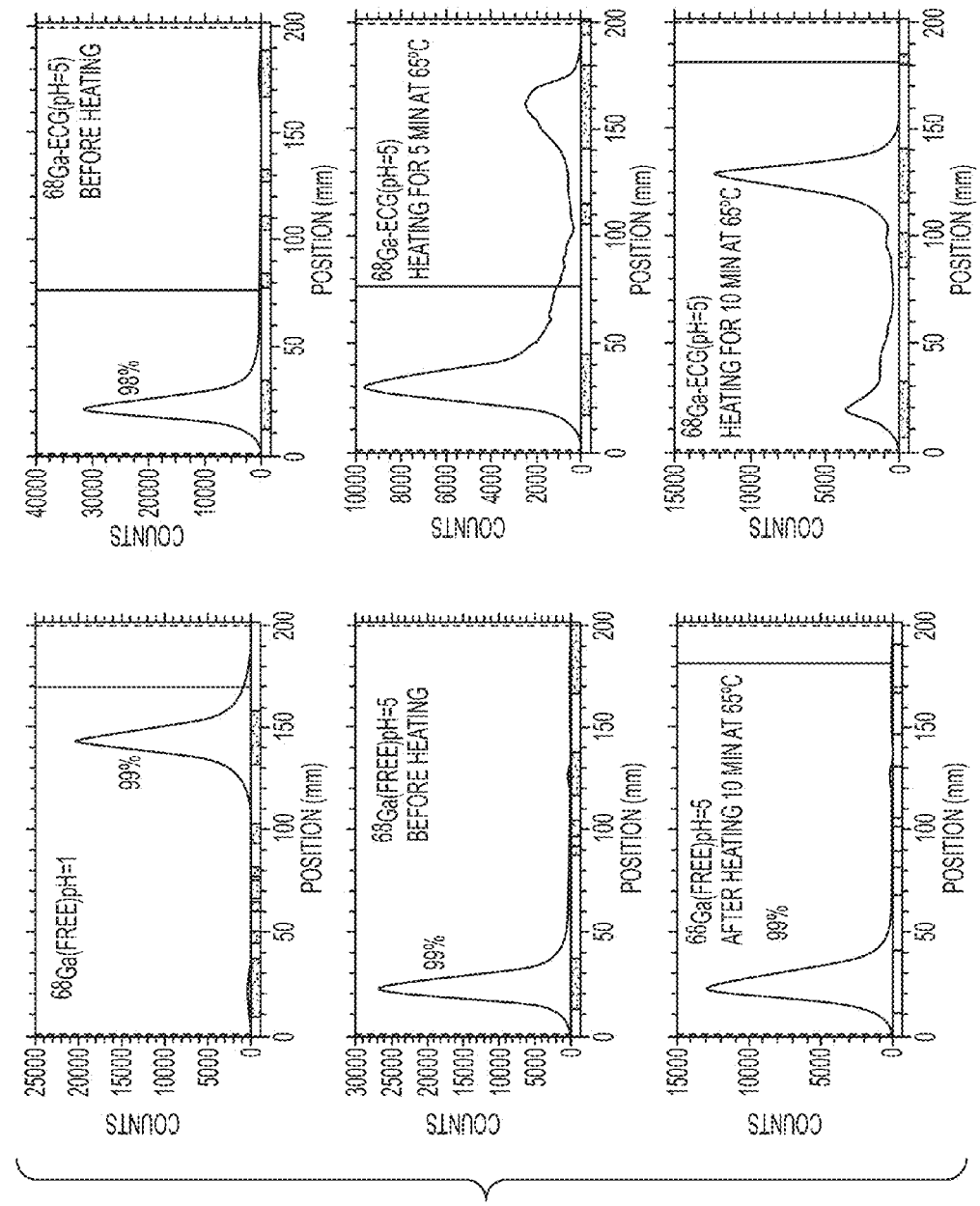
FIG. 2. TLC analysis of $^{68}$Ga-ECG using saline as an eluant. Radio-TLC analysis of the purity of $^{68}$Ga-ECG was >96%.
Figure 3:
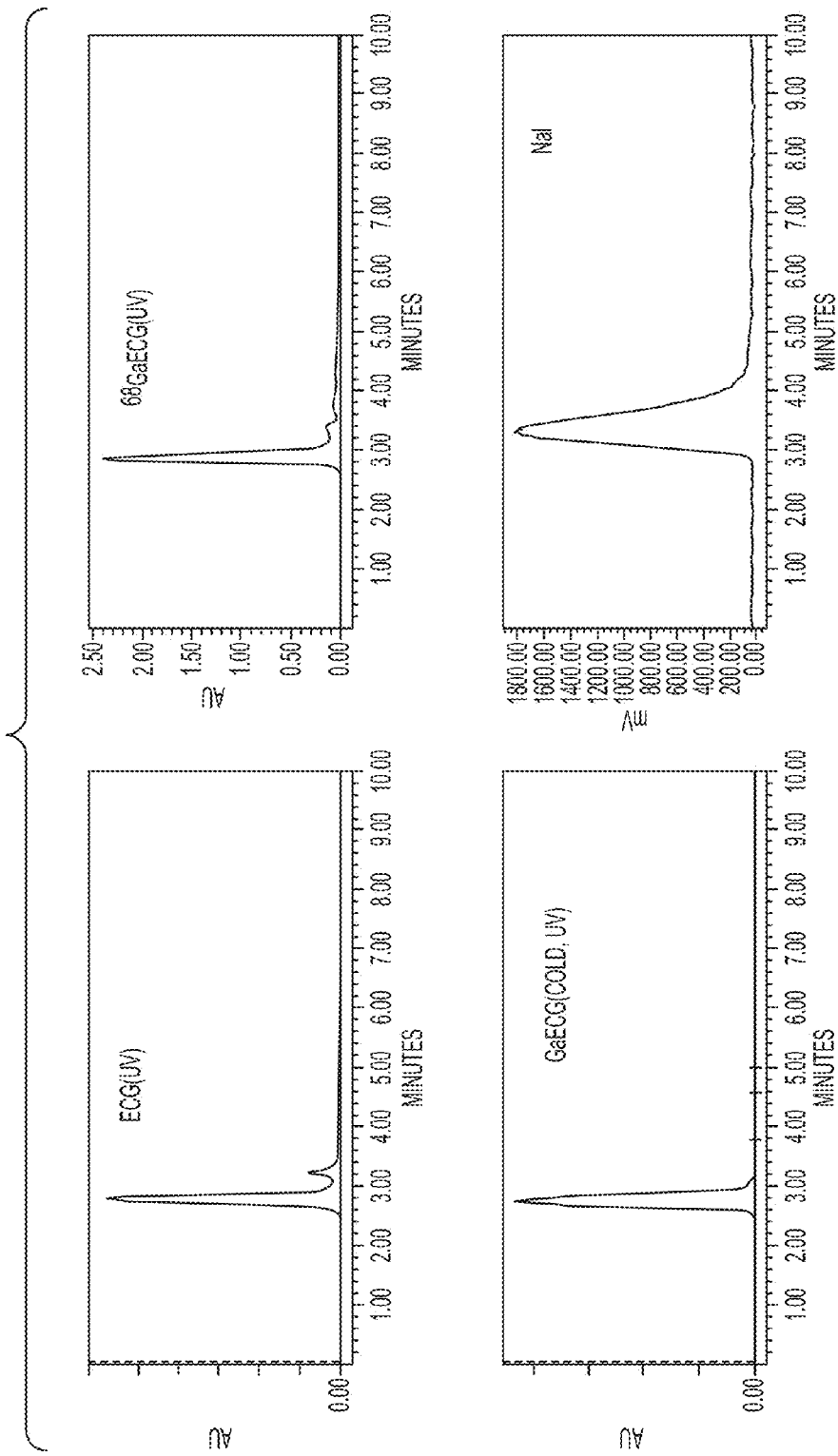
FIG. 3. HPLC analysis of $^{68/69}$Ga-ECG and ECG (Mobile phase: H$_2$O/acetonitrile, 9:1 V/V, flow rate: 0.5 ml/min, column: C18-extend (Agilent), UV ABS 210 nm). HPLC analysis of the purity of $^{68}$Ga-ECG was >96%.
Figure 4A:
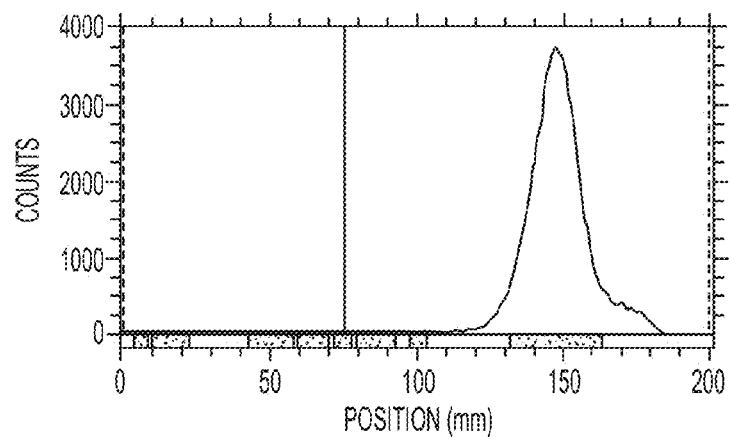
FIG. 4. ITLC (top a, in Saline) and HPLC (bottom b, NaI detector) analysis of $^{99m}$Tc-ECG (mobile phase: H$_2$O/acetonitrile, 9:1 V/V, flow rate: 0.5 ml/min, Column: C18-extend (Agilent), UV ABS: 210 nm). Radio-TLC and HPLC analysis of the purity of $^{99m}$Tc-ECG were >96%.
Figure 4B:
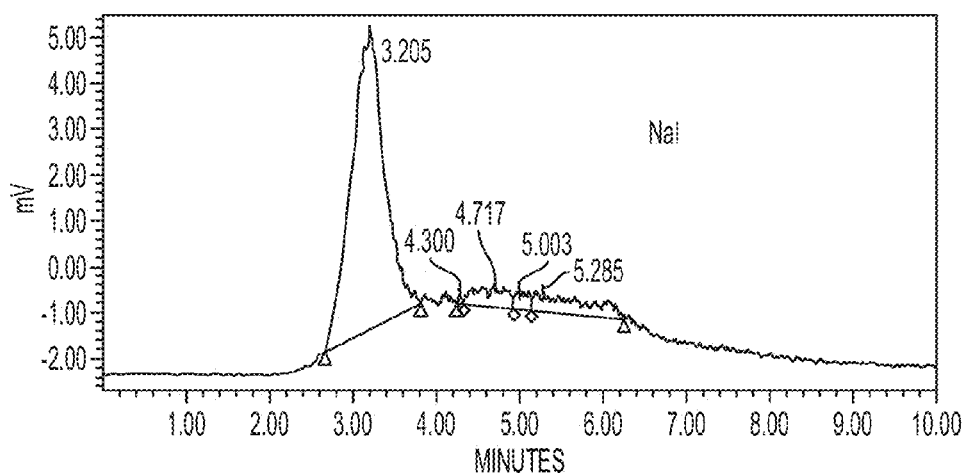

NMR of cold $^{69}$Ga-ECG was $^1H$ NMR ($D_2O$, δ): 2.94-3.38 (m, 8H), 3.43-3.65 (m, 4H), 3.50-3.80 (m, 10H), 3.92-4.02 (t, 2H), 4.23-4.34 (d, 2H), 5.15-5.34(d, 2H), $^{13}C$ NMR($D_2O$, δ): 175.51, 175.16, 95.55, 90.85, 90.67, 75.76, 74.90, 73.55, 71.59, 70.71, 70.66, 70.10, 69.88, 60.72, 60.62, 56.72, 54.11, 23.53, 22.83, 22.16. Radio-TLC and HPLC analysis of the purity of $^{68}$Ga-ECG and $^{99m}$Tc-ECG were >96% (FIGS. 2-4). HPLC of cold $^{69}$Ga-ECG were used to confirm the structure of $^{68}$Ga-ECG (FIG. 3).

Example 3

Radiosynthesis of $^{68}$Ga-ECG and $^{99m}$Tc-ECG $^{68}GaCl_3$ was obtained from a $^{68}$Ge/$^{68}$Ga generator (Eckert Ziegler, Valencia, Calif.) eluted with 0.1N HCl. $^{68}GaCl_3$ (120 μl, 300 μCi) was added to the solution of ECG (1.2 mg) in 0.1 ml $H_2O$, and pH value was adjusted to 4-5 with $NaHCO_3$ (40 μl, 0.1 N). The solution was heated at 60° C. for 15 min. Sodium pertechnetate ($Na^{99m}TcO_4$) was obtained from $^{99}$Mo/$^{99m}$Tc generator by Covidien (Houston, Tex.). Radiosynthesis of $^{99m}$Tc-ECG was achieved by adding $^{99m}$Tc-pertechnetate (40-50 mCi) into the lyophilized residue of ECG (5 mg) and tin (II) chloride ($SnCl_2$, 100 μg). The complexation of ECG with $^{99m}$Tc was carried out at pH 6.5. Radiochemical purity was determined by TLC (Waterman No. 1, Aldrich-Sigma, St. Louis, Mo.) eluted with saline. High-performance liquid chromatography (HPLC), equipped with a NaI detector and UV detector (210 nm), was performed on a C-18 reverse phase column (C18-extend, Agilent, Santa Clara, Calif.) eluted with acetonitrile/water (1:9, V/V) at a flow rate of 0.5 ml/min. HPLC of cold $^{69}$Ga-ECG was used to confirm the structure of $^{68}$Ga-ECG.

Example 4

Biodistribution of Radiotracers in Mesothelioma-Bearing Rats

Female Fischer 344 rats (150±25 g) (Harlan Sprague-Dawley, Indianapolis, Ind.) (n=3 rats/time point) were inoculated with malignant pleural mesothelioma cells derived from the IL-45 cell line. Tumor cells ($10^6$ cells/rat) were injected (i.m.) into the hind legs. Studies were performed 14 to 17 days after inoculation when tumors were approximately 1 cm in diameter. In tissue distribution studies, each animal was injected (i.v., 10 μCi/rat, 10 μg/rat) with $^{99m}$Tc-ECG, $^{68}$Ga-ECG and $^{18}$F-FDG. Rats were sacrificed at 0.5-4 hrs. The selected tissues were excised, weighed and counted for radioactivity by using a gamma counter (Packard Instruments, Downers Grove, Ill.). The biodistribution of tracer in each sample was calculated as percentage of the injected dose per gram of tissue wet weight (% ID/g).

Tumor and tissue uptake (% ID/g) of $^{68}$Ga-ECG, $^{99m}$Tc-ECG and $^{18}$F-FDG are shown in Tables 1-3. The highest tumor uptake of $^{99m}$Tc-ECG is 0.47 at 30 min post injection, and declined to 0.08 at 240 min post injection. Tumor uptake (% ID/g), tumor/lung, tumor/blood and tumor/muscle count density ratios for $^{99m}$Tc-ECG (30-240 min) were 0.47±0.06 to 0.08±0.01; 0.71±0.07 to 0.85±0.04; 0.47±0.03 to 0.51±0.01, and 3.49±0.24 to 5.06±0.25; for $^{68}$Ga-ECG (15-60 min) were 0.70±0.06 to 0.92±0.08; 0.64±0.05 to 1.15±0.08; 0.42±0.03 to 0.67±0.07, and 3.84±0.52 to 7.00±1.42; for FDG (30-180 min) were 1.86±0.22 to 1.38±0.35; 3.18±0.44 to 2.92±0.34, 4.19±0.44 to 19.41±2.05 and 5.75±2.55 to 3.33±0.65, respectively. Higher kidney uptake was observed for both $^{68}$Ga-ECG and $^{99m}$Tc-ECG groups, presumable because EC and EC-conjugates may interact with renal tubules in the kidney (Yang et al., 2003).

Example 5

Scintigraphic Imaging Studies

Female Fischer 344 rats (150±25 g) bearing malignant pleural mesothelioma (at hind legs) derived from the IL-45 cell line were used for imaging studies. Studies were performed 14 to 17 days after inoculation when tumors were approximately 1 cm in diameter. Scintigraphic images were obtained either from a micro-PET (Inveon) embedded in the gantries coordinate PET/CT data acquisition, or from a M-gamma camera (Siemens Medical Systems, Inc., Hoffman Estates, Ill.) equipped with low-energy parallel-hole collimator. Each animal was administered with $^{99m}$Tc-ECG (300 μCi/rat, iv), $^{68}$Ga-ECG and 18F-FDG (400 μCi/rat, iv), and the images were obtained at 0.5-4 hrs. To demonstrate $^{68}$Ga-ECG could be used for image-guided therapy, the same mesothelioma-bearing rats (n=3) at tumor volume 1.5 cm were treated with paclitaxel (20 mg/kg, iv, single injection). Prior to treatment and post-paclitaxel treatment on day 7, the tumor-bearing rats were imaged with $^{68}$Ga-ECG. Computer outlined regions of interest (ROI) (counts per pixel) were used to determine tumor-to-background count density ratios for $^{99m}$Tc-ECG. Computer outlined regions of interest (ROI) (counts per pixel) for tumor and muscle at the corresponding time interval were used to generate a dynamic plot for 68Ga-ECG and 18F-FDG. Dynamic plot was from 0 to 45 minutes. Paclitaxel was selected because it produced antiproliferative effects by inhibition of glucose transporters (Glut-1) in cell line studies (Rastogi et al., 2007). Also, it has been reported that mesothelioma responds to paclitaxel treatment in the animal model (Schulz et al., 2011).

Figure 5:
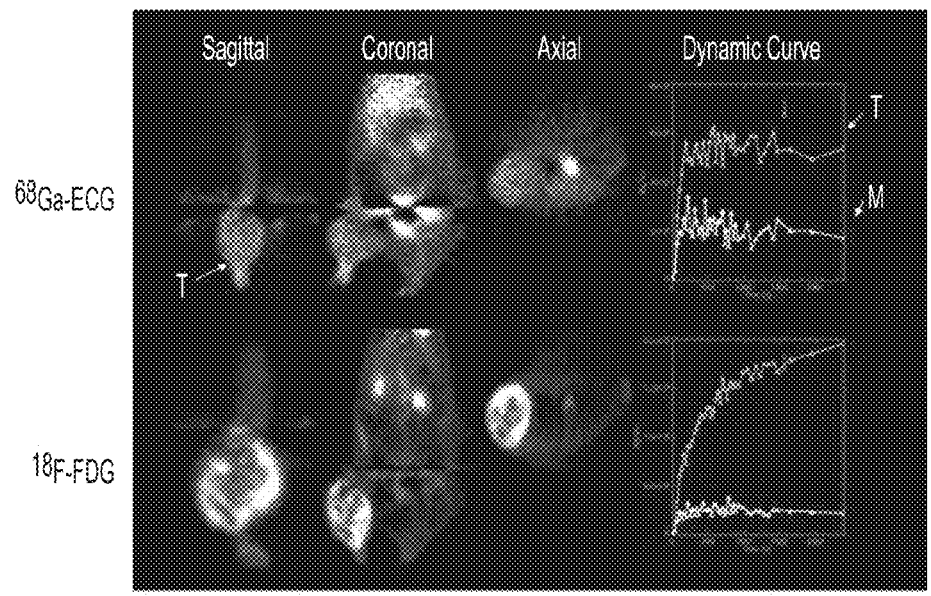
FIG. 5. $^{18}$F-FDG and $^{68}$Ga-ECG PET imaging in mesothelioma-bearing rats (400 µCi/rat, iv, acquired 45 minutes). Computer outlined regions of interest (ROI) (counts per pixel) for tumor and muscle at the corresponding time interval were used to generate a dynamic plot. Dynamic plot was from 0 to 45 minutes.
Figure 6:
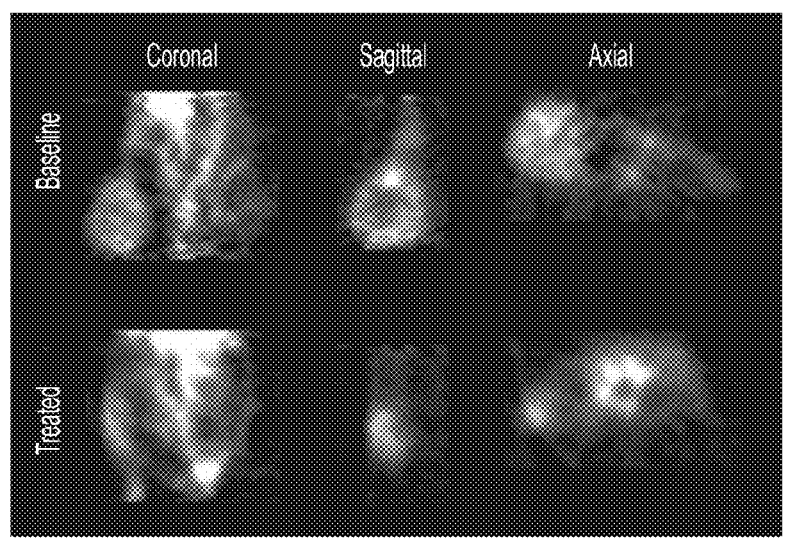
FIG. 6. $^{68}$Ga-ECG PET images in rat bearing mesothelioma (400 µCi/rat, iv, lower body) before and after treatment at 45 minutes. Top: baseline at tumor size 1.5 cm, bottom: treated with paclitaxel (20 mg/kg, iv, single dose on day 7). T: tumor.
Figure 7:
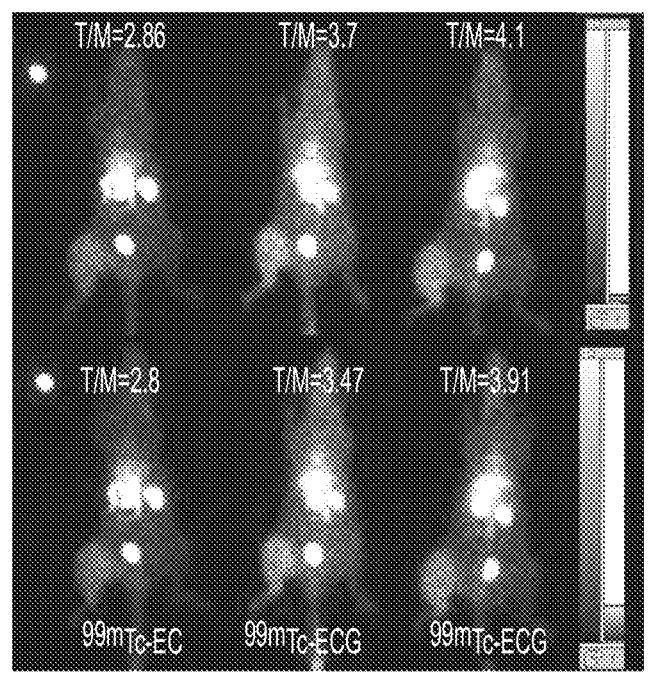
FIG. 7. Planar scintigraphy of $^{99m}$Tc-EC (left) and $^{99m}$Tc-ECG (300 µCi/rat, iv, acquired 500,000 count) (middle and right) in mesothelioma-bearing rats. The numbers are tumor-to-muscle count density ratios at 1 hr (upper panel) and 2 hrs (lower panel). T: tumor.
Figure 8:
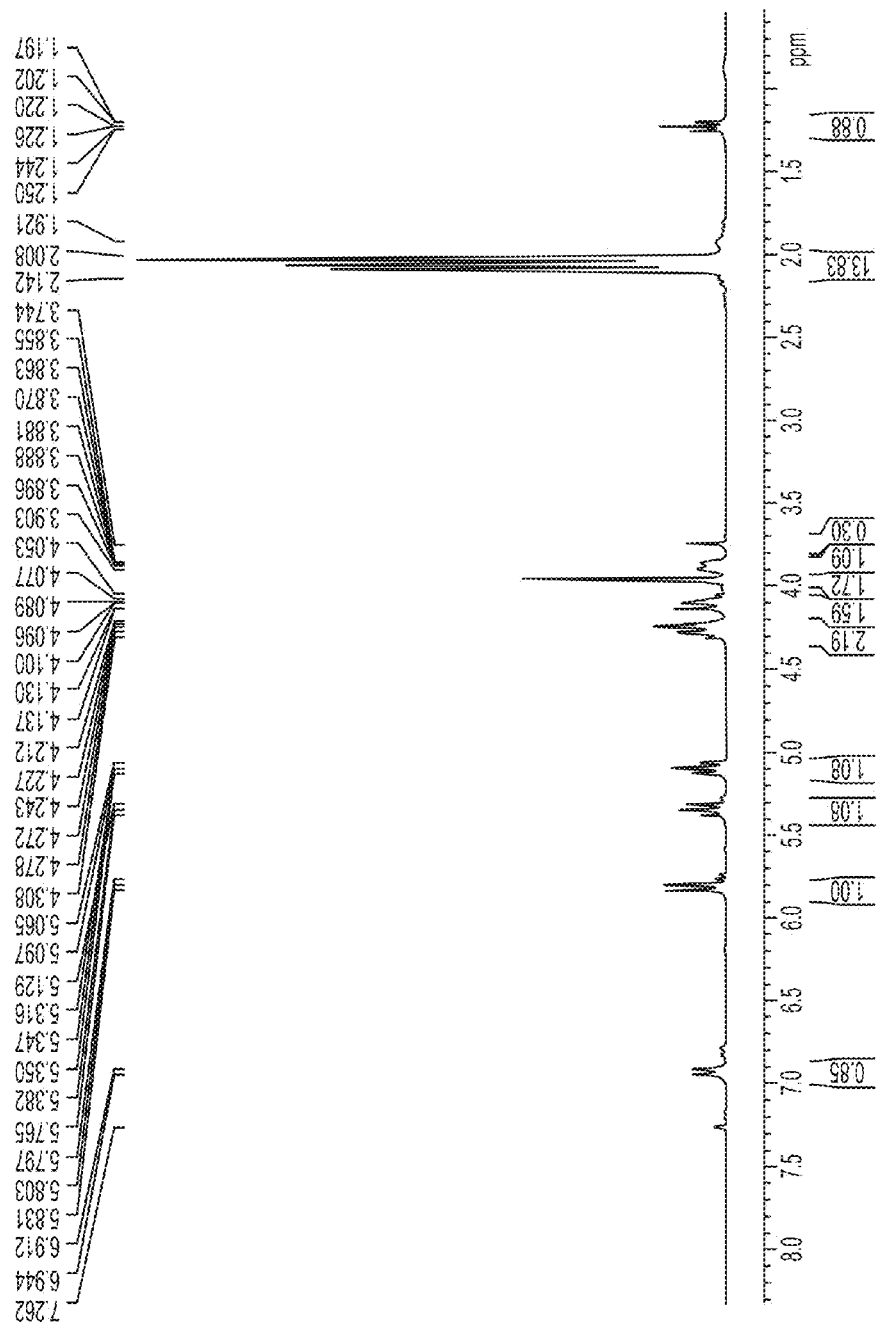
FIG. 8. $^1$H NMR of G-Ac-T
Figure 9:
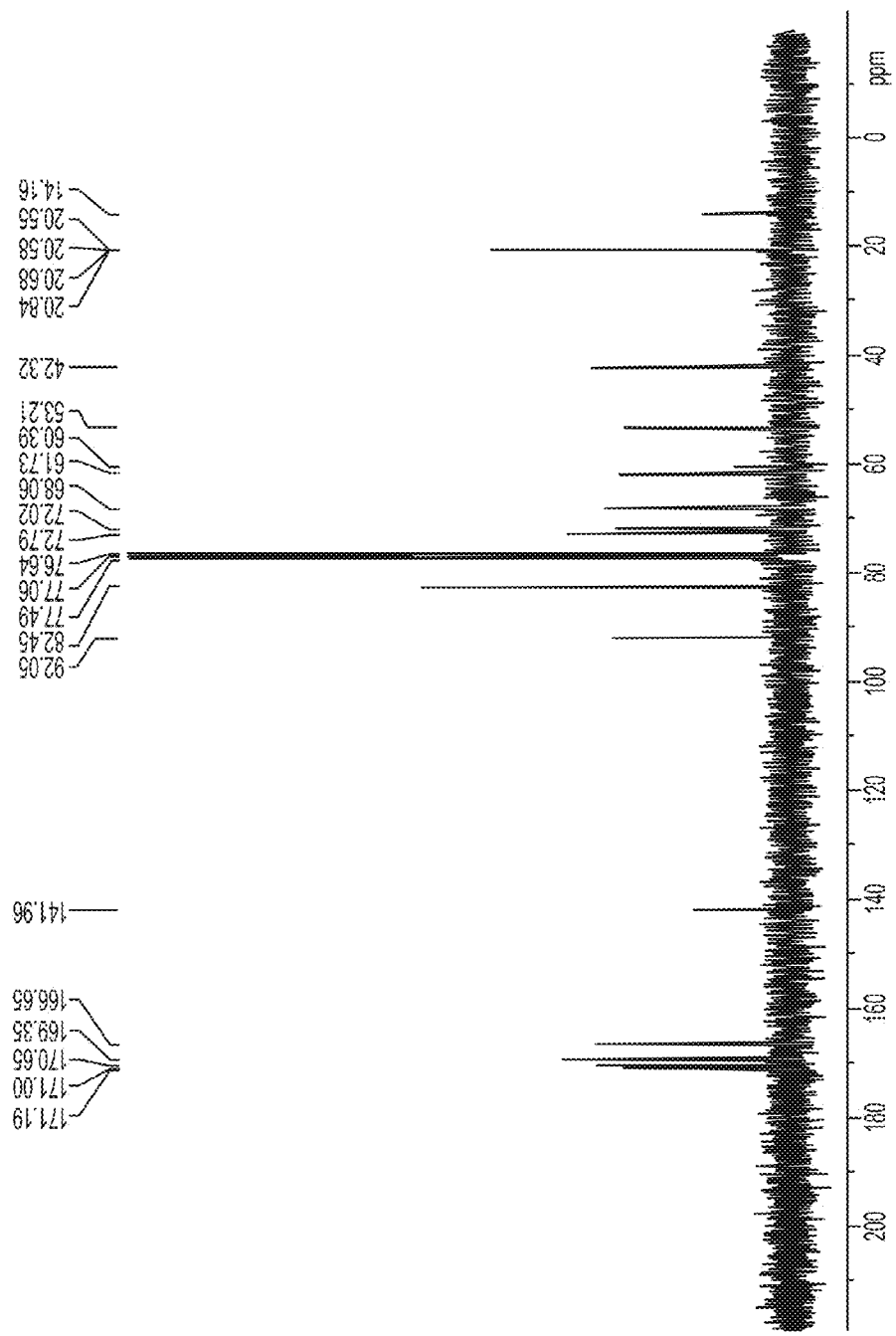
FIG. 9. $^{13}$C NMR of T-G-(Ac)4
Figure 10:
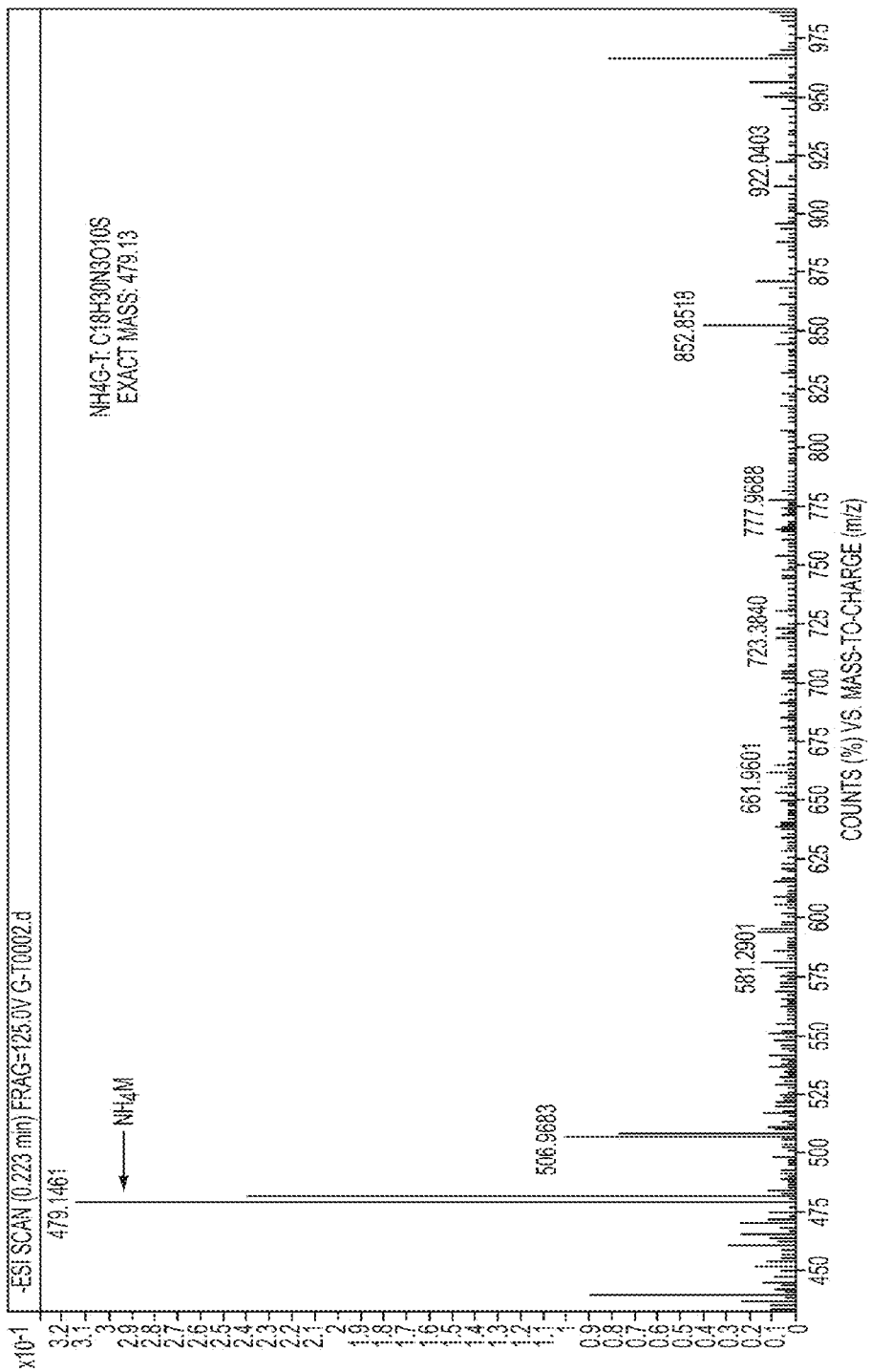
FIG. 10. MS of T-G-(Ac)4
Figure 11:
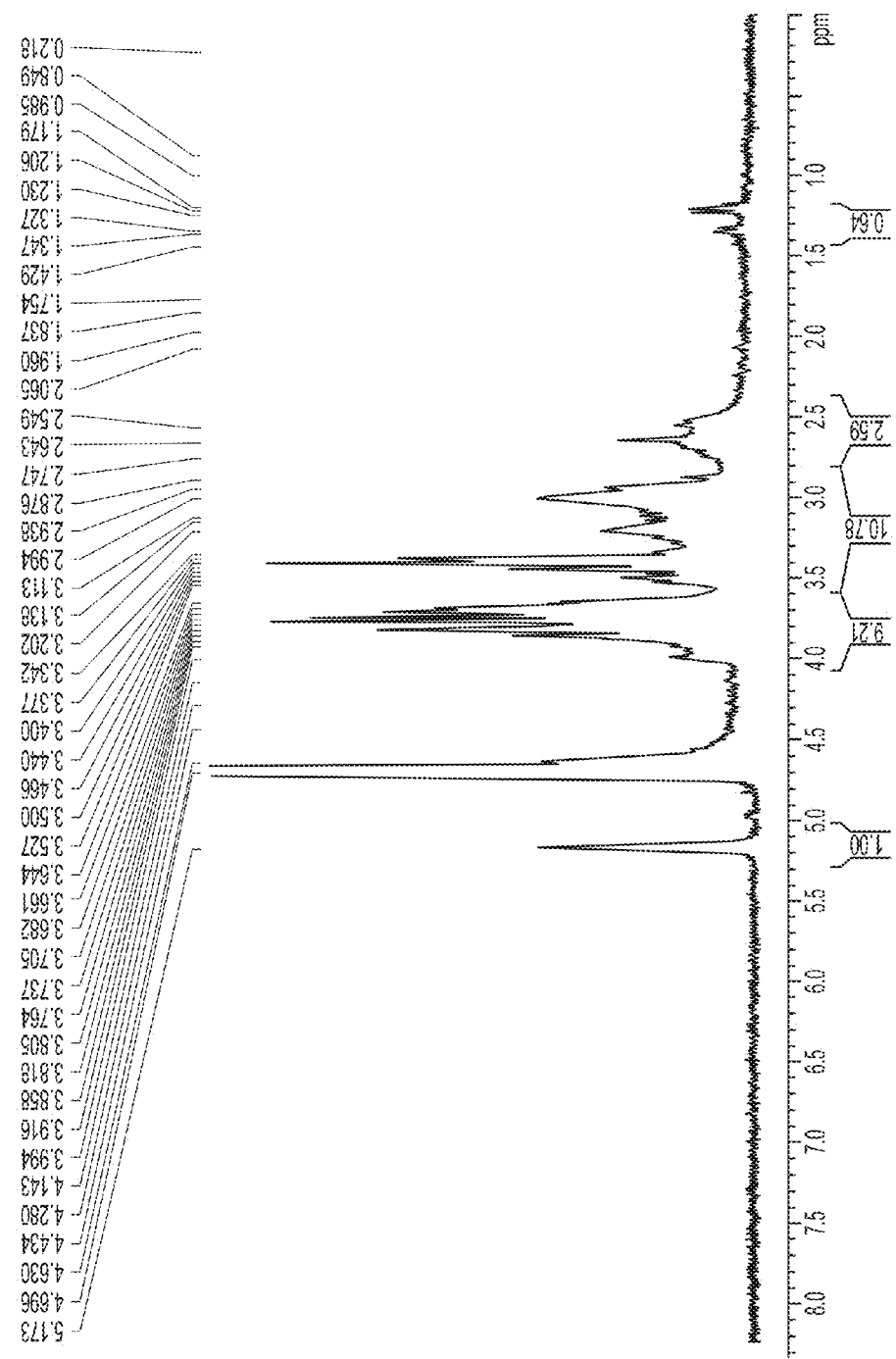
FIG. 11. $^1$H NMR of EC-G
Figure 12:
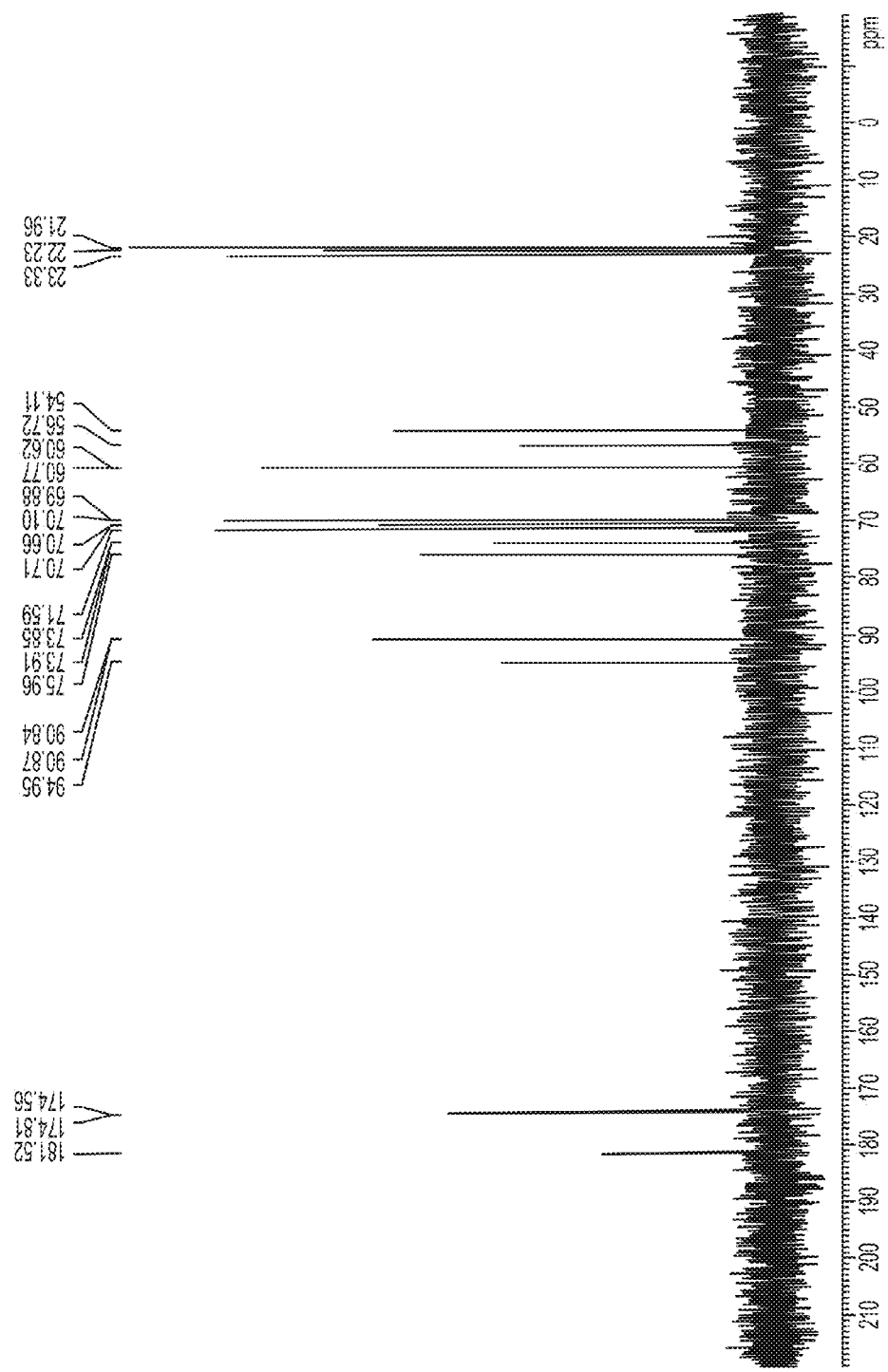
FIG. 12. $^{13}$C NMR of EC-G
Figure 13:
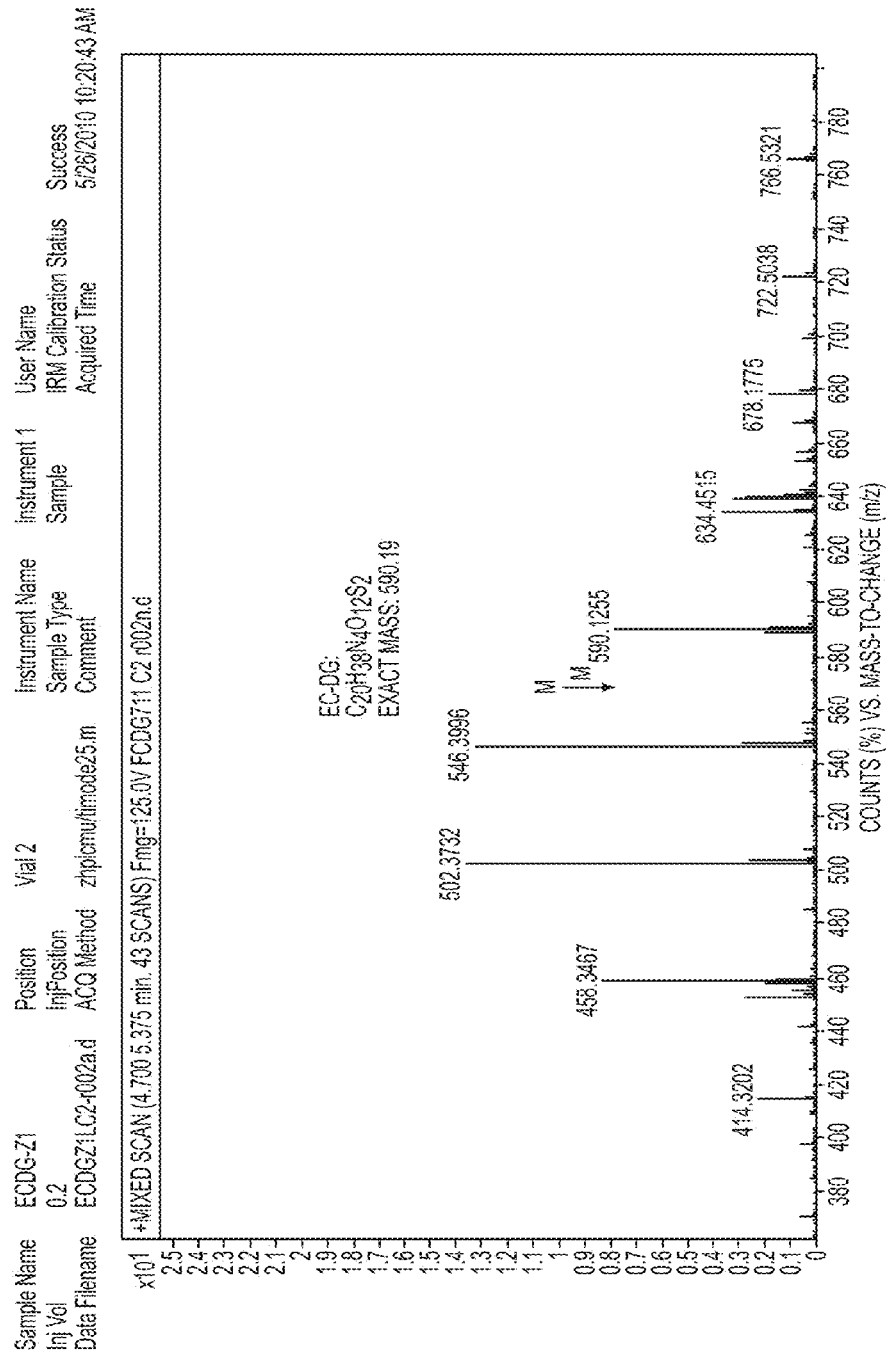
FIG. 13. Mass Spectrum of EC-G
Figure 14:
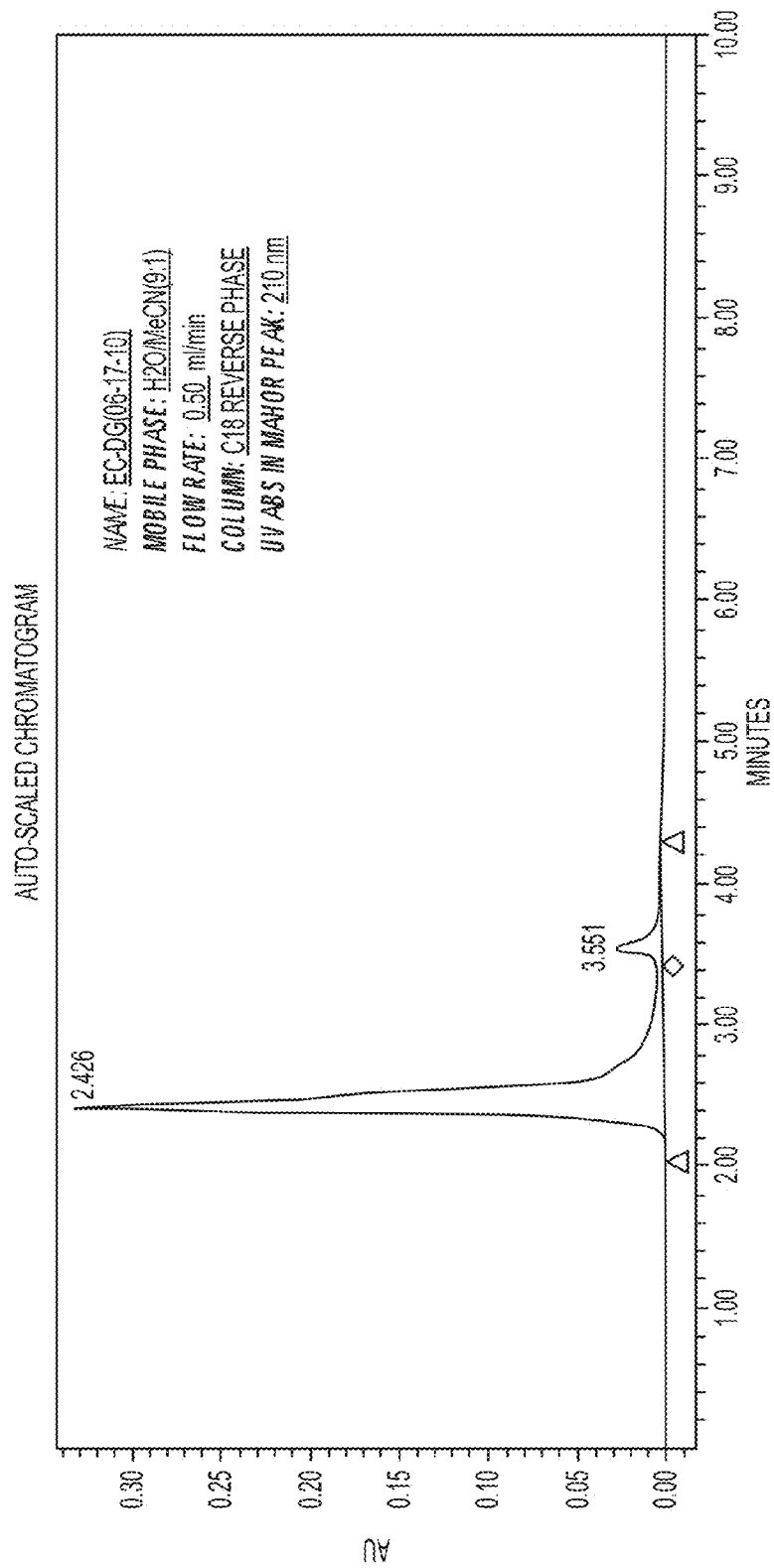
FIG. 14. HPLC of EC-G
Figure 15:
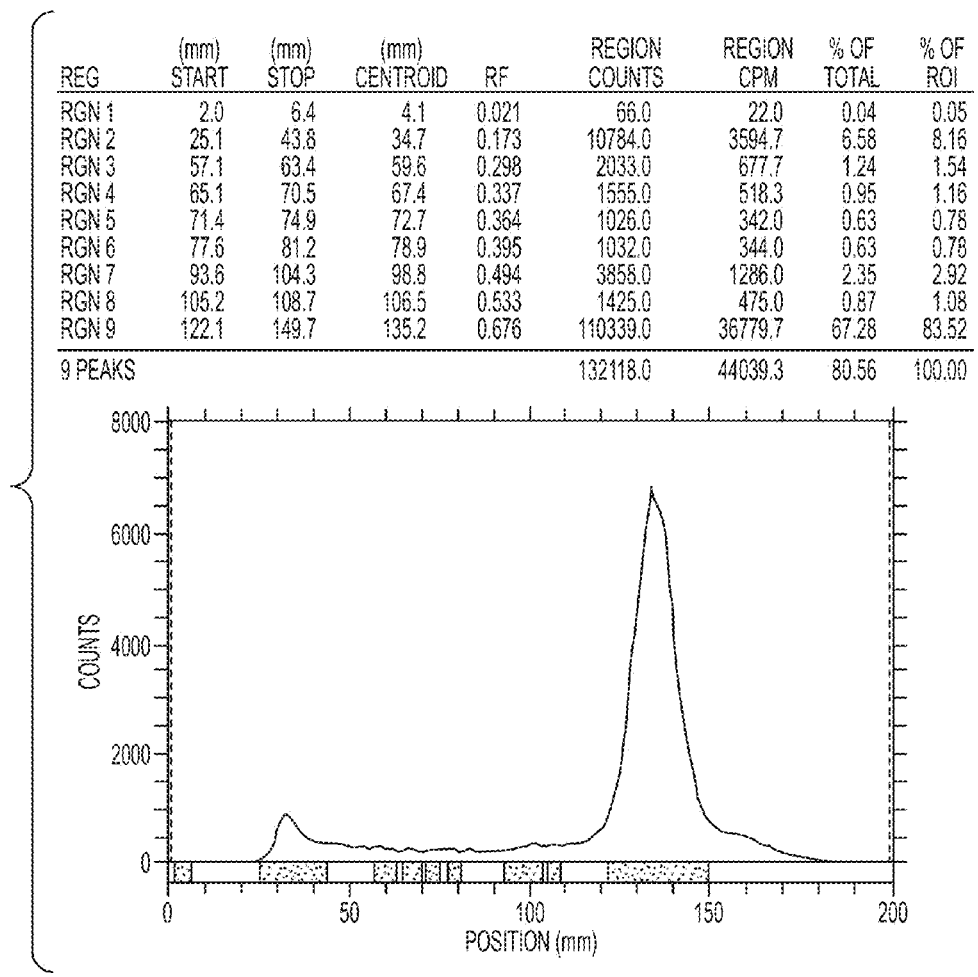
FIG. 15. $^{99m}$TcEC-G (ITLC, using saline as eluant)

Scintigraphic images of rats administered $^{68}$Ga-ECG, $^{99m}$Tc-ECG and $^{18F}$-FDG showed that tumors could be clearly visualized at 0.5-4 hrs (FIGS. 5-7). Dynamic plot of tumor uptake with $^{68}$Ga-ECG and $^{18F}$-FDG showed similar transport pattern (FIG. 5). $^{68}$Ga-ECG was able to monitor paclitaxel treatment response in the same mesothelioma-bearing rats (FIG. 6). Two rats receiving $^{99m}$Tc-ECG (middle and right) were randomly selected to compare to that of the rat receiving $^{99m}$Tc-EC (left) under the same imaging panel. Tumor in $^{99m}$Tc-ECG group showed much higher uptake than $^{99m}$Tc-EC (control) group at 1 and 2 hrs (FIG. 7).

In summary, efficient synthesis of ECG was achieved with high yield. $^{68}$Ga-ECG and $^{99m}$Tc-ECG were prepared with high radiochemical purities. Biodistribution and planar imaging studies demonstrated the pharmacokinetic distribution and feasibility of using $^{68}$Ga-ECG and $^{99m}$Tc-ECG to image mesothelioma. $^{68}$Ga-ECG and $^{99m}$Tc-ECG showed an increased uptake in mesothelioma in the model tested, indicating they are feasible to assess tumor volume. $^{68}$Ga-ECG and $^{99m}$Tc-ECG may be useful for screening, diagnosing, staging and assessing the efficacy of treatment in respect to all cancer types.

Example 6

Manufacturing of EC-G Kit

Figure 16:
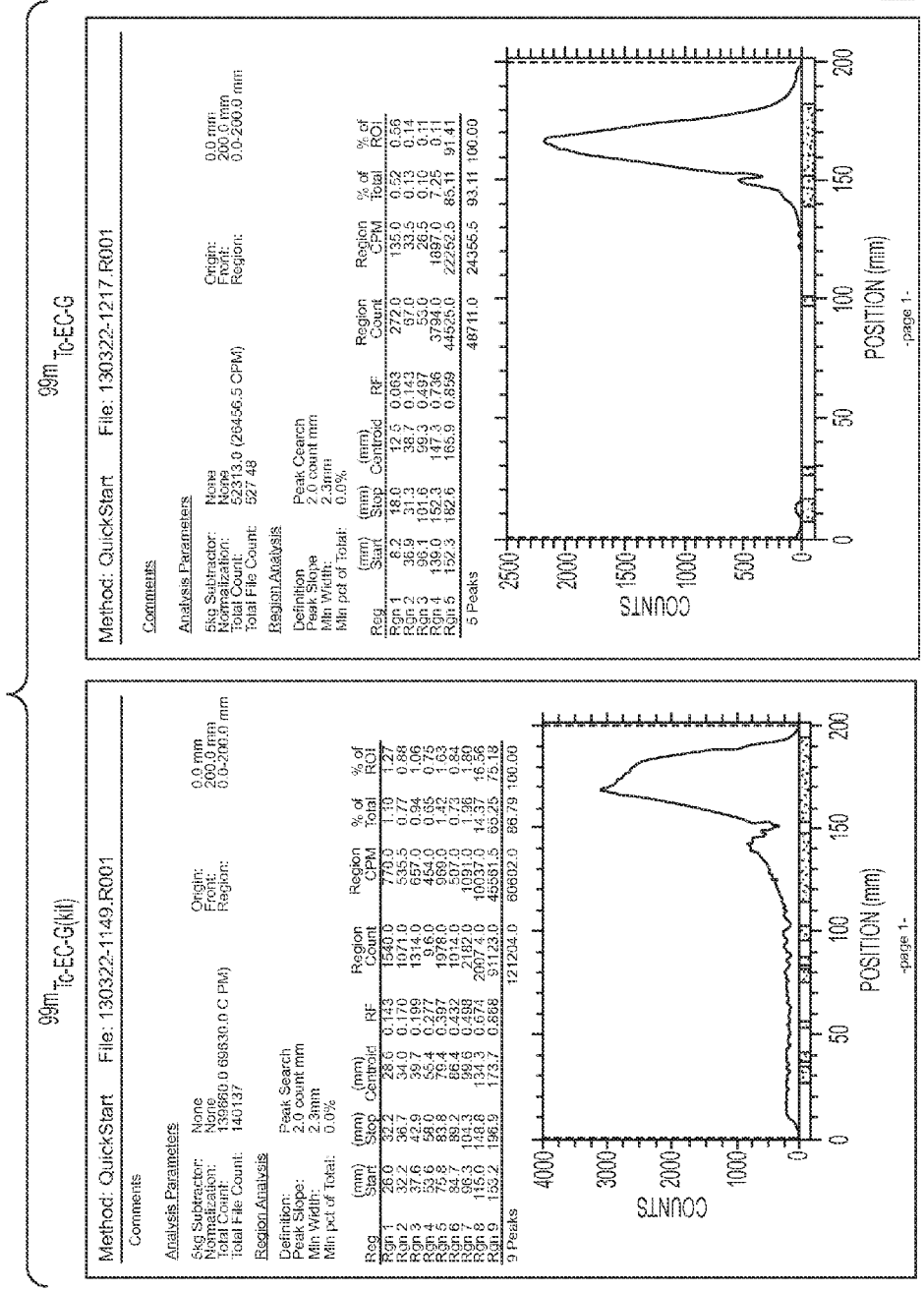
FIG. 16. Instant-thin layer chromatographic analysis of $^{99m}$Tc-EC-G using saline as a mobile phase. Paper: Waterman no. 1; Cat no: 3030614. Left panel is the product made using the kit disclosed herein; right panel is a standard $^{99m}$Tc-EC-G.
Figure 17:
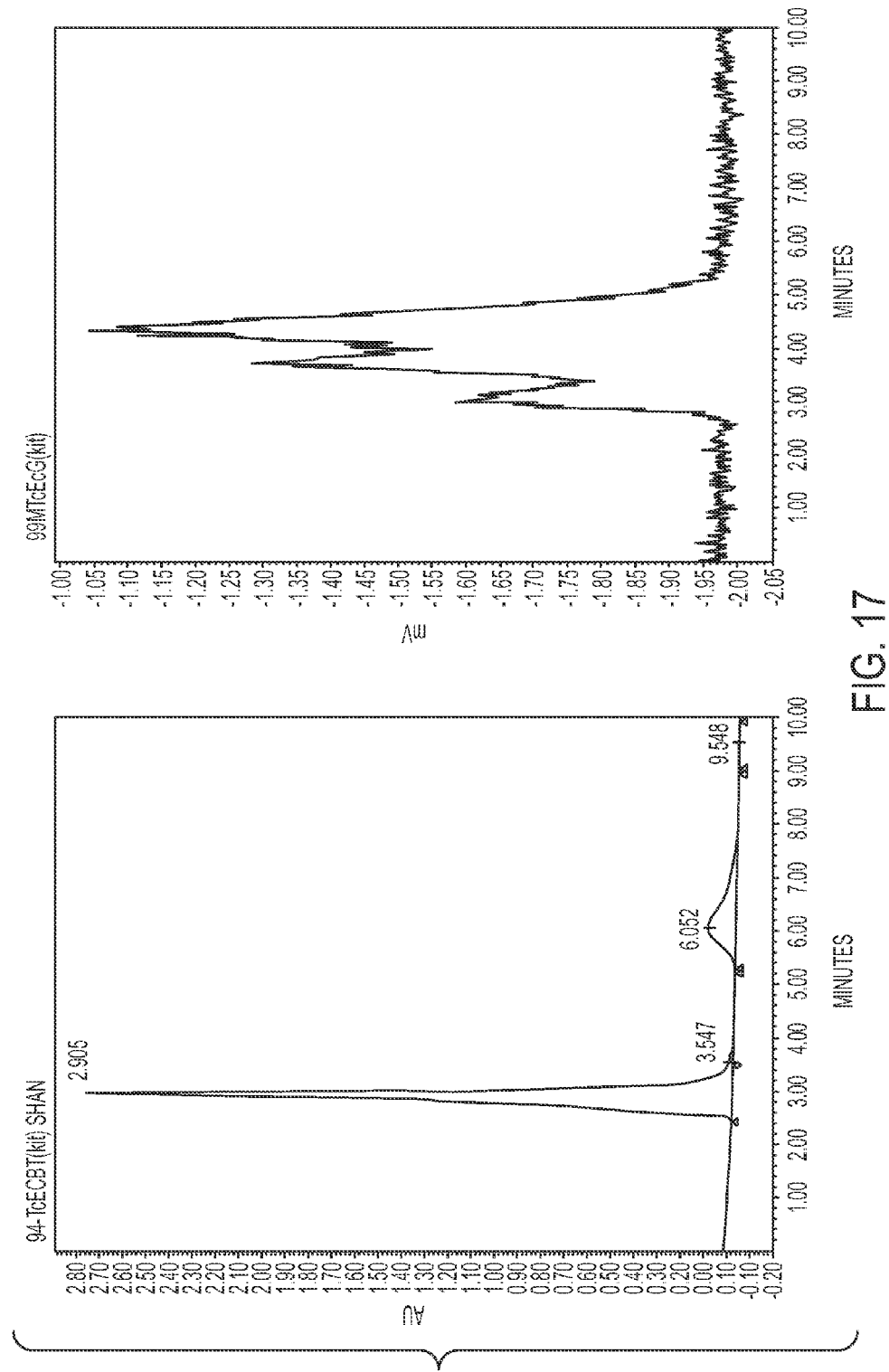
FIG. 17. HPLC analysis of 99 mTc-EC-G made using the kit disclosed herein using H$_2$O/MeCN (9:1) as an eluent at the flow rate of 0.50 mL/min. Column: Extend C18; SN: USFK004129, Agilent).
Figure 18:
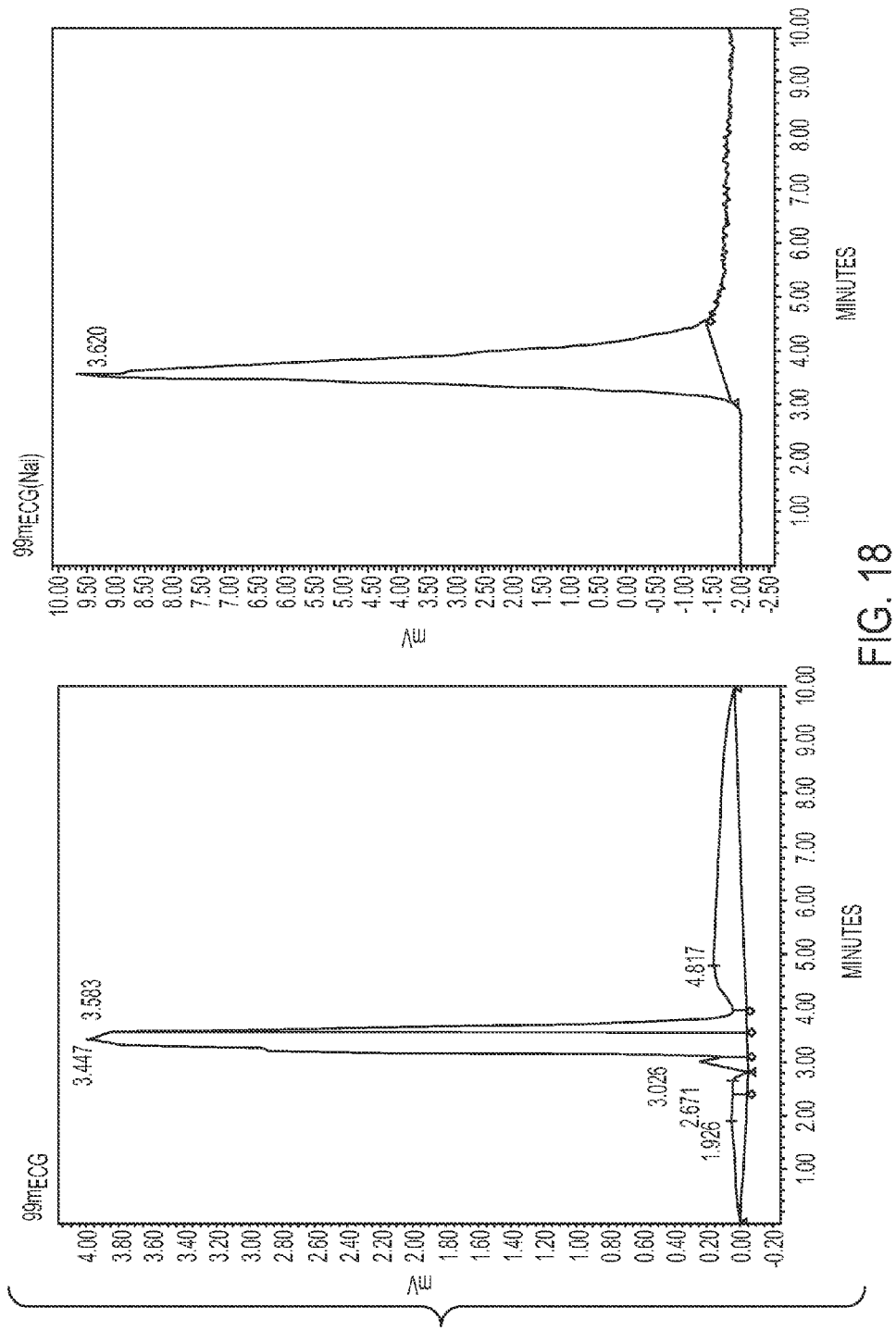
FIG. 18. HPLC analysis of the standard 99 mTc-EC-G using H$_2$O/MeCN (9:1) as an eluent at the flow rate of 0.50 mL/min. Column: Extend C18; SN: USFK004129, Agilent).
Figure 19:
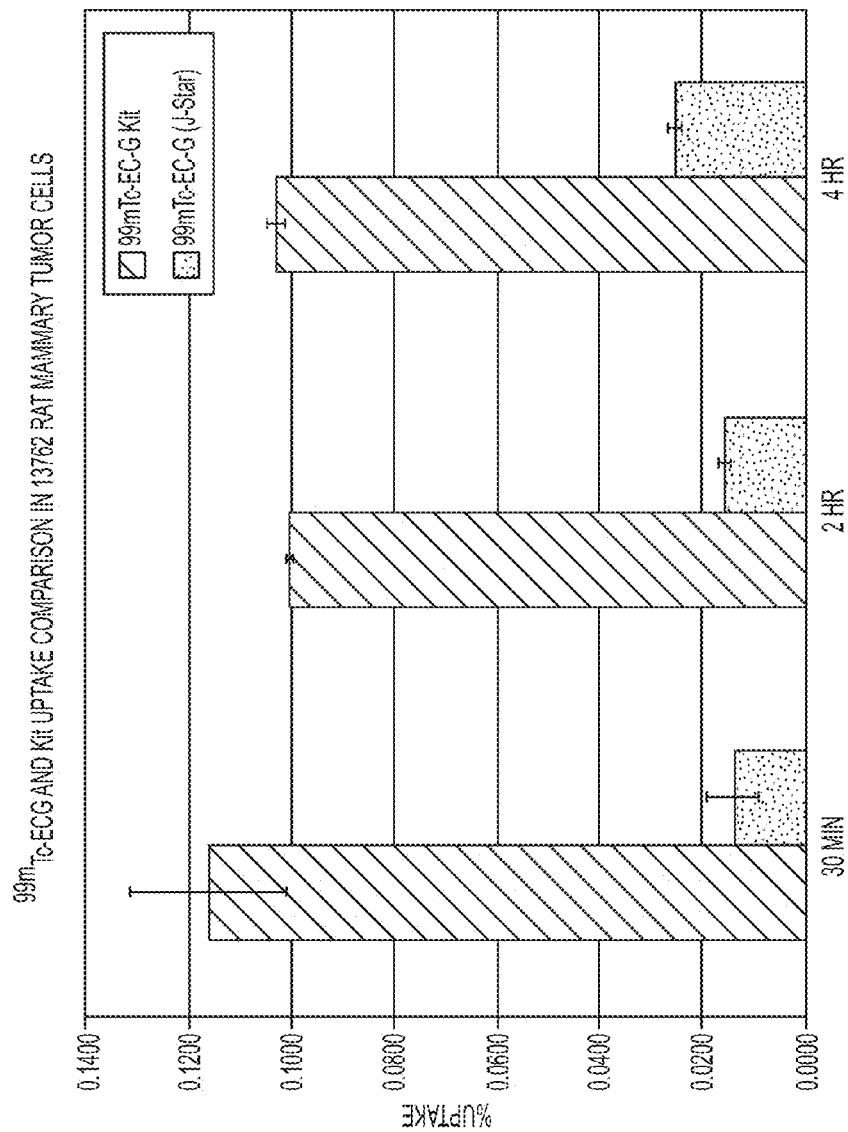
FIG. 19. Uptake of kit-made and standard 99 mTc-EC-G in 13762 rat mammary tumor cells. Left columns are kit product and right columns are standard product.

A single kit EC-G was manufactured by dissolving 1.0 mg EC-G in 0.1 mL water. To this, 1 mg L-ascorbic acid in 0.1 mL water, 0.5 mg Neomycin in 0.1 mL, 0.5 mg L-cysteine, and 0.1 mL of 1 mg/mL Tin(II) chloride solution were added. The product was lyophilized for a single cold kit. $^{99m}$Tc-EC-G made using the kit was analyzed by instant-thin layer chromatography using saline as a mobile phase. The results indicated the same retention for both the kit product as well as a standard $^{99m}$Tc-EC-G product (FIG. 16). The kit product and standard product were also analyzed by HPLC using $H_2O$/MeCN (9:1) as an eluent at a flow rate of 0.50 mL/min (FIGS. 17 and 18). The uptake of the kit product and standard product were analyzed for uptake in 13762 rat mammary tumor cells. The kit product was found to have greater than 5-fold better uptake than the standard product (FIG. 19).

REFERENCES

The following references, to the extent that they provide exemplary, procedural or other details supplementary to those set forth herein, are specifically incorporated herein by reference.

U.S. Publn. 2008/0107198
Alberico et al., *Surg. Oncol. Clin. N. Am.*, 13(1):13-35, 2004.
Bodansky, In: *Peptide Chemistry*, 2$^{nd}$ Ed., Springer-Verlag, New York, 1993.
Grant, In: *Synthetic Peptides*, Freeman & Co., New York, 1992.
Green and Wuts, *Protective Groups in organic Synthesis*, 3$^{rd}$ Ed. Wiley, NY, 1999.
Henson et al., *Am. J. Neuroradiol.*, 25(6):969-972, 2004.
Kundra et al., *J. Nucl. Med.*, 43(3):406-412, 2002.
Rastogi et al., *Cancer Lett.*, 257(2):244-251, 2007.
Remington's Pharmaceutical Sciences, 18th Ed. Mack Printing Company, 1289-1329, 1990.
Saha et al., *Semin. Nucl. Med.*, 24(4):324-349, 1994.
Schulz et al., *Ann. Thorac. Surg.*, 92(6):2007-2013, 2011.
Strunk and Schild, *Eur. Radiol.*, 14(6):1055-1062, 2004.
Yang et al., *Radiology*, 226:465-473, 2003.

What is claimed is:

1. A method of preparing a thiazolidine-sugar conjugate comprising admixing an amino sugar with an unprotected thiazolidine carboxylic acid in the presence of a coupling agent, thereby producing the thiazolidine-sugar conjugate.

2. The method of claim 1, further comprising reducing the thiazolidine-sugar conjugate with a reducing agent comprising an alkali metal and an electron source to thereby provide an ethylenedicysteine-sugar conjugate.

3. The method of claim 1, wherein the amino sugar is an amino hexose or an amino pentose.

4. The method of claim 3, wherein the amino hexose is an amino derivative of glucose, galactose, mannose, idose, talose, altrose, allose, gulose or fructose.

5. The method of claim 4, wherein the amino hexose is glucosamine.

6. The method of claim 3, wherein the amino pentose is an amino derivative of ribose, xylose, arabinose or lyxose.

7. The method of claim 1, wherein the amino sugar is a sugar having an amino group positioned at the 2' position of the sugar.

8. The method of claim 1, wherein hydroxyl groups of the amino sugar are protected.

9. The method of claim 8, wherein the amino sugar is 1,3,4,6-tetra-O-acetyl-2-amino-α-D-glucopyranose hydrochloride.

10. The method of claim 1, wherein the admixing is carried out in an organic solvent.

11. The method of claim 10, wherein the organic solvent is dimethylformamide, dimethylsulfoxide, dioxane, methanol, ethanol, hexane, methylene chloride, acetonitrile, tetrahydrofuran, or a mixture thereof.

12. The method of claim 2, further comprising purifying the thiazolidine-sugar conjugate prior to the reduction.

13. The method of claim 12, wherein the thiazolidine-sugar conjugate is purified by silica gel column chromatography, HPLC, or a combination thereof.

14. The method of claim 2, wherein the alkali metal is lithium, sodium or potassium.

15. The method of claim 2, wherein the electron source is liquid ammonia, methylamine, ethylamine, ethylenediamine, or combinations thereof.

16. The method of claim 2, further comprising chelating a metal ion to the ethylenedicysteine-sugar conjugate to generate a metal ion labeled- ethylenedicysteine(EC)-sugar conjugate.

17. The method of claim 16, wherein the metal ion is selected from the group of metal ions consisting of a technetium ion, a stannous ion, a copper ion, an indium ion, a thallium ion, a gallium ion, an arsenic ion, a rhenium ion, a holmium ion, a yttrium ion, a samarium ion, a selenium ion, a strontium ion, a gadolinium ion, a bismuth ion, an iron ion, a manganese ion, a lutecium ion, a cobalt ion, a platinum ion, a calcium ion and a rhodium ion.

18. The method of claim 16, wherein the metal ion is a radionuclide.

19. The method of claim 18, wherein the radionuclide is selected from the group consisting of $^{99m}$Tc, $^{117m}$Sn, $^{177}$Lu, $^{188}$Re, $^{186}$Re, $^{153}$Sm, $^{166}$Ho, $^{90}$Y, $^{89}$Sr, $^{67}$Ga, $^{68}$Ga, $^{111}$In, $^{183}$Gd, $^{59}$Fe, $^{225}$Ac, $^{212}$Bi, $^{211}$At, $^{45}$Ti, $^{60}$Cu, $^{61}$Cu, $^{67}$Cu, $^{64}$Cu, and $^{62}$Cu.

20. The method of claim 16, wherein the metal ion is a non-radioactive metal.

21. The method of claim 20, wherein the non-radioactive metal is $^{187}$Re.

* * * * *